(12) United States Patent
Hierse et al.

(10) Patent No.: US 8,067,625 B2
(45) Date of Patent: Nov. 29, 2011

(54) FLUOROSURFACTANTS

(75) Inventors: Wolfgang Hierse, Gross-Zimmern (DE); Nikolai (Mykola) Ignatyev, Duisburg (DE); Martin Seidel, Darmstadt (DE); Elvira Montenegro, Weinheim (DE); Peer Kirsch, Yokohama Kanagawa (JP); Andreas Bathe, Darmstadt (DE)

(73) Assignee: Merck Patent Gesellschaft Mit Beschrankter Haftung, Darmstadt (DE)

( * ) Notice: Subject to any disclaimer, the term of this patent is extended or adjusted under 35 U.S.C. 154(b) by 198 days.

(21) Appl. No.: 12/307,291

(22) PCT Filed: Jul. 2, 2007

(86) PCT No.: PCT/EP2007/005839
§ 371 (c)(1),
(2), (4) Date: Jan. 2, 2009

(87) PCT Pub. No.: WO2008/003444
PCT Pub. Date: Jan. 10, 2008

(65) Prior Publication Data
US 2009/0264525 A1 Oct. 22, 2009

(30) Foreign Application Priority Data
Jul. 4, 2006 (DE) .......... 10 2006 031 149

(51) Int. Cl.
*C07C 51/60* (2006.01)
*C07H 15/00* (2006.01)
(52) U.S. Cl. .......... 554/231; 554/30; 554/108; 554/172; 554/227; 554/225; 536/18.2; 536/18.5; 536/119; 508/459; 508/485; 508/520
(58) Field of Classification Search .......... None
See application file for complete search history.

(56) References Cited

U.S. PATENT DOCUMENTS

| | | | |
|---|---|---|---|
| 1,985,424 A | 12/1934 | Alfred |
| 2,703,798 A | 3/1955 | Schwartz |
| 2,708,798 A | 5/1955 | Warner et al. |
| 3,048,569 A | 8/1962 | Harris |
| 3,311,599 A | 3/1967 | Shumate |
| 3,359,319 A | 12/1967 | Fawcett |
| 3,522,293 A | 7/1970 | Furguson |
| 3,720,644 A | 3/1973 | Haszeldine |
| 3,787,423 A | 1/1974 | Bolhofer et al. |
| 3,847,961 A | 11/1974 | Koshar |
| 4,242,516 A | 12/1980 | Mueller |
| 4,292,402 A | 9/1981 | Pollet et al. |
| 4,324,741 A | 4/1982 | Umemoto |
| 5,560,995 A | 10/1996 | Usuki et al. |
| 5,691,299 A | 11/1997 | Fabry |
| 6,110,976 A | 8/2000 | Hansen et al. |
| 6,137,011 A | 10/2000 | Marhold et al. |
| 6,175,041 B1 | 1/2001 | Takasaki et al. |
| 6,582,849 B1 | 6/2003 | Heider |
| 6,706,881 B2 | 3/2004 | Damon et al. |

| | | | |
|---|---|---|---|
| 2004/0137385 A1 | 7/2004 | Orem et al. |
| 2007/0135662 A1 | 6/2007 | Nardello et al. |
| 2009/0075594 A1 | 3/2009 | Shichino et al. |
| 2009/0197201 A1 | 8/2009 | Hierse et al. |
| 2009/0312432 A1 | 12/2009 | Hierse et al. |
| 2009/0320718 A1 | 12/2009 | Hierse et al. |
| 2010/0152081 A1 | 6/2010 | Hierse et al. |

FOREIGN PATENT DOCUMENTS

| | | |
|---|---|---|
| DE | 691 26 789 | 2/1998 |
| DE | 199 08 943 | 9/2000 |
| DE | 199 41 566 | 3/2001 |
| DE | 10 2005 000 858 A1 | 7/2006 |

(Continued)

OTHER PUBLICATIONS

English, et al., Characterizatin of Photooxidized Self-assembled Monolayers and Bilayers by Spontaneous Desorption Mass Spectrometry, 2000, Analytical Chemistry, vol. 72, No. 24, pp. 5973-5980 (8 pages).*
Falbe, J., Surfactants in Consumer Products, 1987, Springer Verlag, Brlin, (10 pages).*
Kirsch, P., Modern Florroorganic Chemistry, 2004, Wiley VCH pp. 67-72 & 144-145 (9 pages).*
Kaine, K. et al., A convenient systhesis of trifluoromethyl ethers by oxidaiton desulfurization-fluorinaitn of dithiocarbonates, 2000, Bull. Chem. soc. JPn., 73, 471-484 (14 pages).*
Dorwald, F.A., Side Reactions in Organic Synthesis, 2005, Wiley VCH, Weinheim pp. 1-15.*

(Continued)

*Primary Examiner* — Andrew D Kosar
*Assistant Examiner* — Yate K Cutliff
(74) *Attorney, Agent, or Firm* — Millen, White, Zelano & Branigan, P.C.

(57) ABSTRACT

The present invention relates to fatty acid esters of polyols or sulfonated fatty acid esters or sulfonated fatty acid amides containing at least one group Y, where Y stands for $CF_3$—$(CH_2)_a$—O—, $SF_5$—, $CF_3$—$(CH_2)_a$—S—, $CF_3CF_2S$—, $[CF_3$—$(CH_2)_a]_2N$— or $[CF_3$—$(CH_2)_a]NH$—, where a stands for an integer selected from the range from 0 to 5, or formula (I), where Rf stands for $CF_3$—$(CH_2)_r$—, $CF_3$—$(CH_2)_r$—O—, $CF_3$—$(CH_2)_r$—S—, $CF_3CF_2$—S—, $SF_5$—$(CH_2)_r$— or $[CF_3$—$(CH_2)_r]_2N$—, $[CF_3$—$(CH_2)_r]NH$— or $(CF_3)_2N$—$(CH_2)_r$—, B stands for a single bond, O, NH, NR, $CH_2$, C(O)—O, C(O), S, $CH_2$—O, O—C(O), N—C(O), C(O)—N, O—C(O)—N, N—C(O)—N, O—$SO_2$ or $SO_2$—O, R stands for alkyl having 1 to 4 C atoms, b stands for 0 or 1 and c stands for 0 or 1, q stands for 0 or 1, where at least one radical from b and q stands for 1, and r stands for 0, 1, 2, 3, 4 or 5, to processes for the preparation of these compounds, and to uses of these surface-active compounds.

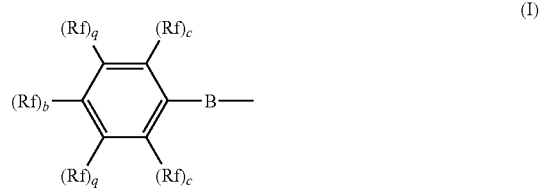

(I)

22 Claims, No Drawings

FOREIGN PATENT DOCUMENTS

| | | |
|---|---|---|
| EP | 0 015 592 A1 | 9/1980 |
| EP | 0 558 515 | 9/1993 |
| EP | 1 081 129 | 3/2001 |
| EP | 1 228 062 | 8/2002 |
| EP | 1 296 182 A1 | 3/2003 |
| EP | 1386920 | 2/2004 |
| GB | 809 060 | 2/1959 |
| JP | 56169666 | 12/1981 |
| JP | 57 108064 | 7/1982 |
| JP | 62-270555 A | 11/1987 |
| JP | 1070444 | 3/1989 |
| JP | 6470443 | 3/1989 |
| JP | 64070444 | 3/1989 |
| JP | 10-301379 | 11/1998 |
| JP | 2000 072735 | 3/2000 |
| JP | 2001 133984 | 5/2001 |
| JP | 2001 294568 | 10/2001 |
| JP | 2003 267900 | 9/2003 |
| JP | 2005077961 | 3/2005 |
| WO | WO-92 06984 | 4/1992 |
| WO | WO-98 14540 | 4/1998 |
| WO | WO-99 19344 | 4/1999 |
| WO | WO-01 36410 | 5/2001 |
| WO | WO 03/010128 A2 | 2/2003 |
| WO | WO-2004 067692 | 8/2004 |
| WO | WO-2004 078990 | 9/2004 |
| WO | WO-2005 035472 | 4/2005 |
| WO | WO 2006/072401 A1 | 7/2006 |
| WO | WO-2007 060839 | 5/2007 |
| WO | WO-2008 003447 | 1/2008 |

OTHER PUBLICATIONS

Yoshizaki, H. et al., The first total synthesis of Re lipopolysaccharide, 2000, Nippon Kagakkai, abstract (20 pages).*

A. Chwala et al., "Handbuch der Textilhilfsmittel, Verlag Chemie", New York 1977, Kapitel 3.24, S. 735 ff.

G. Kennedy et al. "The Toxicology of Perfluorooctanoate", Critical Reviews of Toxicology, vol. 34, No. 4 (2004) pp. 351-384.

XP-002458072—Database Accession No. 2000-805382.

XP-002458073—Database Accession No. 1988: 509861.

XP-002458074—Database Accession No. 2785147, 2786929.

XP-002458075—Database Accession No. 7735809, 7738271.

XP-002458076—Database Accession No. 5843062, 5841578, 5839854, 5835796.

XP-002458077—Database Accession No. 1678484, 1678483.

XP-002458078—Database Accession No. 1985:187077.

J. G. Riess et al., "Carbohydrate- and Related Polyol-Derived Fluorosurfactants : An Update", Carbohydrate Research, vol. 327 (2000) pp. 147-168.

"7.2. Ethoxylates," Ullmann-Surfactants, Jan. 24, 2006, pp. 59-67.

"Perfluoroalkyl-substituted Alkanoic Acids," Database Caplus [online]. Retrieved from STN Database accession No. 1982:471949. abstract., Jan. 17, 2008.

Abe, T. et al., "The Electrochemical Fluorination of Nitrogen-Containing Carboxylic Acids. Fluorination of Methyl Esters of 3-diakylamino Propionic Acids," Journal of Fluorine Chemistry, 1992, vol. 57, pp. 101-111.

Abstract, Claims, and Background of the Invention for "Hair-treatment formulations." Retrieved from http://www.free-patent-search.net/Hair-Treatment/hair-treatment-71.htm on Jun. 20, 2006.

Agency of Ind Science & Technol., "Novel perfluoroalkenylamine and production thereof," Patent Abstract of Japan, Publication Date: Mar. 15, 1989; English Abstract of JP-64 070444.

Agency of Ind Science & Techonology, "Novel nitrogen-containing perfluoropropenes and production thereof," Patent Abstract of Japan, Publication Date: Mar. 15, 1989; English Abstract of JP-64 070443.

Alexander, E. S. et al., "Polyfluoroalkyl Compounds of Silicon. Part IX. Silanes containing the Bis(trifluoromethyl)amino-group," Journal of the Chemical Society, Section A: Inorganic, Physical and Theoretical Chemistry, 1970, pp. 2285-2291.

Alexander, E. S. et al., "Polyfluoroalkyl Derivatives of Nitrogen. XXXVII. Reactions of N, N-bis (trifluoromethyl)Vinylamine," Journal of the Chemical Society [Section] C: Organic 1968, vol. 7, pp. 796-801.

Banks, R. E. et al., "Nitroxide Chemistry. Part IV. Reaction of Bistrifluoromethyl Nitroxide with Aldehydes," Journal of Chemical Society, 1973, pp. 80-82.

Beilstein Ref: 4-03-00-00276 (Reg. # 1737836), 1959.

Beilstein Ref: 4-03-00-00276 (Reg. # 1745846), 1959.

Beilstein Ref: 4-03-00-00276 (Reg. # 1754890), 1957.

Beilstein Ref: 5-04 (Reg. # 1908404), 1969,.

Beilstein Ref: 5-04 (Reg. # 2364247), 1964.

Beilstein Ref: 5-04,6-04 (Reg. #2043866), 1971.

Beilstein Ref: 6-03 (Reg. # 6380369), 1988.

Beilstein Ref: 6-04 (Reg. # 4994102), 1980.

Central Glass Co Ltd., "Method for producing optically active alpha-methyl-bis-3,5-(Tri-fluotomethyl) Benzylamine," Patent Abstracts of Japan, Publication Date: Oct. 23, 2001; English Abstract of JP-2001 294568.

Coy, D. H. et al., "Polyfluoroalkyl Derivatives of Nitrogen. Part XXXVIII. Reaction of N-Bromobistrifluoromethylamine with Allyl Chloride; Preparation of NN-Bistrifluoromethylprop-2-enylamine," Journal of the Chemical Society, Perkin Translations 1, Chemical Society, 1971, pp. 1062-1065.

Crimmins, M. et al., "Asymmetric Total Synthesis of (+)-Milbemycin D," Journal of the American Chemical Society, vol. 118, 1996, pp. 7513-7528.

Database WPI Week 200534. Derwent Publications Ltd. Mar. 24, 2005.

Fawcett, F. S. et al., "Organic and Biological Chemistry," Journal of the American Chemical Society, 1962, vol. 22, pp. 4275-4285.

Fernandes, T. R. et al., "Organosilicon Chemistry. Part 21. Reactions of NN-bistrifluoromethylamino-oxyl and Perfluoro (2,4-dimethyl-3-oxa-2, 4-diazapentane) with Vinylsilanes, and Pyrolysis of the Resulting Adducts," Journal of the Chemical Society, Dalton Transactions: Inorganic Chemistry, 1978, vol. 9, pp. 1024-1031.

Fleming, G. L. et al., "Polyfluotoalkyl Derivatives of Nitrogen. XXX Reaction of N-chlorobis (trifluoromethyl)Amine with Propene and Vinyl Fluoride and of N-iodobis(trifluoromethyl)Amine with Vinyl Fluoride Under Ionic Conditions," Journal of the Chemical Society [Section] C: Organic 1971, vol. 22, pp. 3829-3833.

Freear, J. et al., "Fluorinated acetylenes. I. Preparation of N, N-bisfluoromethylethynylamines," Journal of the Chemical Socieity [Section] C: Organic 1968: 1096-1103, XP-002465066.

Haas, A. et al., "Catalytic addition of trihalogenomethanesulfenyl Chlorides to olefinic compounds," Journal of Fluroine Chemistry, 1985, pp. 203-210.

Harris, J. F., "Free-radical reactions of fluoroalkanesulfenyl halides. II. Free-radical reactions of trifluoromethanesulfenyl chloride with alkanes," Journal of Organic Chemistry, Database CAPLUS on STN, 1966, vol. 31. No. 3, pp. 931-935.

Haszeldine, Robert N. et al., "Polyfluoroalkyl Derivatives of Nitrogen. Part 44. The Reactions of N-bromobis (trifluoromethyl)Amine with Open-chain, 1, 3-dienes and Cyclohexene under Ionic Conditions," Journal of the Chemical Society, 1980, vol. 2, pp. 372-377.

Hayashi, E. et al., "Decompositions and Removal of Fluorine-containing Carboxylic Acid or its Salt, Used e.g. as Surfactants, Involves Adjusting Temperature of Alkali Conditions of Acid or Salt, Decomposing and Removing Fluorine," Derwent Publications Ltd., Publication Date: Sep. 25, 2003: English Abstract of JP 2003 267900.

Hayashi, E. et al., "Method for decomposing and removing fluorine-containing carboxylic acid or its salts," National Institute of Advanced Industrial Science and Technology, Japan, Sep. 25, 2003, XP-002465054.

Hayashi, E. et al., "New Fluorine-containing Oligomer—With Repeating Units of Formula (1) and (2)," Agency of Ind Sci & Technology, Publication Date: Mar. 7, 2007; English Abstract of JP-2000 072735.

Hayashi, E. et al., "Study on the Preparation and Solution Property of Fluroine-Containing Oligomeric Surfactants by the Use of Nitrogen-containing Perfluorocarboxylic Acids," Journal of the Japan Society of Colour Material, 1999, pp. 765-770, XP-009094640.

Hildreth, James E. K., "N-D-Gluco-N-methylalkanamide compounds, a new class of non-ionic detergents for membrane biochemistry," Biochem. J., 1982, vol. 207, pp. 363-366.

International Search Report for PCT/EP2007/005840 dated Oct. 16, 2007.

International Search Report of PCT/EP2007/005838 dated Aug. 22, 2007.

Knepper, T. P. et al., "Surfactants: Properties production, and environmental aspects," Comprehensive Analytical Chemistry XL, 2003, Chapter 1, pp. 1-49.

Knunyants, L. et al., "An unusual reaction of alpha-cyano-alpha-hydroperfluoroalkyl phosphate with Amines," Mendeleev Chemical Journal, 1977, pp. 15-105.

Konica Minolta Medical & Graphic Inc., "Silver Halide Color Photosensitive Material," Patent Abstracts of Japan, Publication Date: Mar. 24, 2005; English Abstract of JP-2005 077961.

Kraus, G. A. et al., "Model Studies for the Synthesis of Quassinoids. 1. Construction of the BCE Ring System," Journal of Organic Chemistry, 1980, vol. 45, pp. 1175-1176.

Kuhle, E. et al., "Fluorietre Isocyanate und deren Derivate als Zwischenprodukte fur biologisch active Wirkstoffe," Agnew Chem, 1977, vol. 89, pp. 797-804.

Mancuso, A. J. et al., "Oxidation of Long-chain and related alcohols of carbonyls by dimethyl sulfoxide activated by oxalyl chloride," Journal of Organic Chemistry, 1978, vol. 43, No. 12, pp. 2480-2482.

Mita Industrial Co Ltd., "Toner Replenishment Device for image forming device and toner cartridge used therefore," Patent Abstracts of Japan, Publication Date: Nov. 13, 1998; English Abstract of JP10-301379.

Motornyi, S. P. et al., "New esters of N-trifluoromethylcarbamic Acids," Zh. Obshch. Khim., 1959, vol. 29, pp. 2122-2124.

Munavalli, S. et al., "Unusual reactions of trifluoromethylsulfenyl chloride and trifluoromethylthiocopper with five membered heterocyclic compounds," Database CAPLUS on STN,1998, pp. 167-176.

Munavalli, S. et al., "Trifluoromethylthiocopper catalyzed oxirane ring opening," Phosphorus, Sulfer and Silicon and the Related Elements, 2004, vol. 179, No. 8, pp. 1657-1671.

Nelson, D. J. et al., "Simplified Method of Ascertaining Steric Effects in Electrophilic Addition Reactions. A Comparison of Bromination; Oxymercuration and Hydroboration," Journal of the American Chemcial Society, 1989 pp. 1414-1418.

Petrov, K. A. et al., "Synthesis of Secondary Amines with a Trifluoromethyl Group," Zh. Obshsch. Khim., 1959, vol. 29, pp. 2135-2139.

Sagami Chem Res Center, "Perfluoroalkyl substituted alkylcarbosylic acid," Patent Abstract of Japan, Publication Date: Dec. 26, 1981; English Abstract of JP-56 169666.

Sagami Chem Res Center, "Perfluoroalkylthio Compound," Patent Abstracts of Japan, Publication Date: Jul. 5, 1982; English Abstract of JP-57 108064.

Shinetsu Chemical Co. Ltd., "Antireflection film material and pattern forming method," Patent Abstracts of Japan, Publication Date: May 18, 2001; English Abstract of JP2001-133984.

Szonyi, F. et al., "Monodisperse non-ionic fluoroalkyl surfactants," Journal of Fluorine Chemistry, 1987, vol. 36, No. 2, pp. 195-209.

\* cited by examiner

FLUOROSURFACTANTS

The present invention relates to fatty acid esters of polyols or sulfonated fatty acid esters or sulfonated fatty acid amides containing at least one group Y, where Y stands for $CF_3-(CH_2)_a-O-$, $SF_5-$, $CF_3-(CH_2)_a-S-$, $CF_3CF_2S-$, $[CF_3-(CH_2)_a]_2N-$ or $[CF_3-(CH_2)_a]NH-$, where a stands for an integer selected from the range from 0 to 5 or

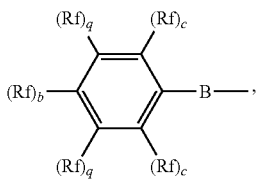

where
Rf stands for $CF_3-(CH_2)_r-$, $CF_3-(CH_2)_r-O-$, $CF_3-(CH_2)_r-S-$, $CF_3CF_2-S-$, $SF_5-(CH_2)_r-$ or $[CF_3-(CH_2)_r]_2N-$, $[CF_3-(CH_2)_r]NH-$ or $(CF_3)_2N-(CH_2)_r-$, B stands for a single bond, O, NH, NR $CH_2$, $C(O)-O$, $C(O)$, S, $CH_2-O$, $O-C(O)$, $N-C(O)$, $C(O)-N$, $O-C(O)-N$, $N-C(O)-N$, $O-SO_2$ or $SO_2-O$, R stands for alkyl having 1 to 4 C atoms, b stands for 0 or 1 and c stands for 0 or 1, q stands for 0 or 1, where at least one radical from b and q stands for 1, and r stands for 0, 1, 2, 3, 4 or 5, to processes for the preparation of these compounds, and to uses of these surface-active compounds.

Fluorosurfactants have an outstanding ability to reduce surface energy, which is utilised, for example, in the hydrophobicisation of surfaces, such as textile impregnation, hydrophobicisation of glass, or de-icing of aircraft wings.

In general, however, fluorosurfactants contain perfluoroalkyl substituents, which are degraded in the environment by biological and other oxidation processes to give perfluoroalkanecarboxylic acids and -sulfonic acids. These are regarded as persistent and are in some cases suspected of causing health damage (G. L. Kennedy, Jr., J. L. Butenhoff, G. W. Olsen, J. C. O'Connor, A. M. Seacat, R. G. Perkins, L. B. Biegel, S. R. Murphy, D. G. Farrar, Critical Reviews in Toxicology 2004, 34, 351-384). In addition, relatively long-chain perfluoroalkanecarboxylic acids and -sulfonic acids accumulate in the food chain.

There is therefore a demand for surface-active substances which have a property profile comparable to the classical fluorosurfactants and which can preferably be degraded oxidatively or reductively. Particularly advantageous compounds here are those which do not leave behind any persistent organofluorine degradation products on degradation.

The Omnova company markets polymers whose side chains contain terminal $CF_3$ or $C_2F_5$ groups. International patent application WO 03/010128 describes perfluoroalkyl-substituted amines, acids, amino acids and thioether acids which contain a $C_{3-20}$-perfluoroalkyl group.

JP-A-2001/133984 discloses surface-active compounds containing perfluoroalkoxy chains which are suitable for use in antireflection coatings. JP-A-09/111,286 discloses the use of perfluoropolyether surfactants in emulsions.

However, these known fluorosurfactants ultimately result in the formation of persistent perfluoroalkanesulfonic acids and -carboxylic acids on degradation. Even the substitutes containing a terminal $CF_3$ group which have been introduced as being more ecologically friendly can be degraded to give persistent trifluoroacetic acid.

The earlier German Patent Application DE 102005000858 describes compounds which carry at least one terminal pentafluorosulfuranyl group or at least one terminal trifluoromethoxy group and contain a polar end group, are surface-active and are highly suitable as surfactants.

Fatty acid esters of polyols and sulfonated fatty acid esters which contain no F atoms are known as surfactants. These fatty acid esters of polyols are used, for example, as emulsifiers for foods and in cosmetics.

This class of fatty acid esters of polyols or sulfonated fatty acid esters or sulfonated fatty acid amides containing $OCF_3$ or $SF_5$ groups as modification was not described in DE 102005000858.

There continues to be a demand for further, preferably degradable substitutes for perfluorinated surfactants.

It has now been found that the novel fatty acid esters of polyols or sulfonated fatty acid esters or sulfonated fatty acid amides containing at least one group Y, where Y stands for $CF_3-(CH_2)_a-O-$, $SF_5-$, $CF_3-(CH_2)_a-S-$, $CF_3CF_2S-$, $[CF_3-(CH_2)_a]_2N-$ or $[CF_3-(CH_2)_a]NH-$, where a stands for an integer selected from the range from 0 to 5 or

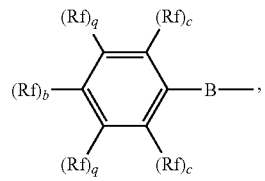

where
Rf stands for $CF_3-(CH_2)_r-$, $CF_3-(CH_2)_r-$, $CF_3-(CH_2)_r-S-$, $CF_3CF_2-S-$, $SF_5-(CH_2)_r-$ or $[CF_3-(CH_2)_r]_2N-$, $[CF_3-(CH_2)_r]NH-$ or $(CF_3)_2N-(CH_2)_r-$, B stands for a single bond, O, NH, NR, $CH_2$, $C(O)-O$, $C(O)$, S, $CH_2-O$, $O-C(O)$, $N-C(O)$, $C(O)-N$, $O-C(O)-N$, $N-C(O)-N$, $O-SO_2$ or $SO_2-O$, R stands for alkyl having 1 to 4 C atoms, b stands for 0 or 1 and c stands for 0 or 1, q stands for 0 or 1, where at least one radical from b and q stands for 1, and r stands for 0, 1, 2, 3, 4 or 5, are surface-active and are highly suitable as surfactants.

The invention therefore relates firstly to fatty acid esters of polyols or sulfonated fatty acid esters or sulfonated fatty acid amides containing at least one group Y, where Y stands for $CF_3-(CH_2)_a-O-$, $SF_5-$, $CF_3-(CH_2)_a-S-$, $CF_3CF_2S-$, $[CF_3-(CH_2)_a]_2N-$ or $[CF_3-(CH_2)_a]NH-$, where a stands for an integer selected from the range from 0 to 5 or

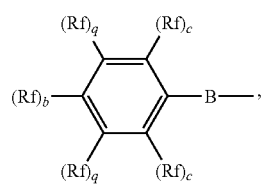

where

Rf stands for $CF_3$—$(CH_2)_r$—, $CF_3$—$(CH_2)_r$—O—, $CF_3$—$(CH_2)_r$—S—, $CF_3CF_2$—S—, $SF_5$—$(CH_2)_r$— or $[CF_3$—$(CH_2)_r]_2N$—, $[CF_3$—$(CH_2)_r]NH$— or $(CF_3)_2N$—$(CH_2)_r$—, B stands for a single bond, O, NH, NR, $CH_2$, C(O)—O, C(O), S, $CH_2$—O, O—C(O), N—C(O), C(O)—N, O—C(O)—N, N—C(O)—N, O—$SO_2$ or $SO_2$—O, R stands for alkyl having 1 to 4 C atoms, b stands for 0 or 1 and c stands for 0 or 1, q stands for 0 or 1, where at least one radical from b and q stands for 1, and r stands for 0, 1, 2, 3, 4 or 5.

The compounds according to the invention preferably contain no further fluorinated groups besides the fluorinated groups Y mentioned.

The fatty acid esters according to the invention are derived from fatty acids, which may be saturated or unsaturated and contain 4 to 25 C atoms, preferably 8 to 22 C atoms, particularly preferably 12 to 20 C atoms. The fatty acids may also carry, for example, OH groups in the side chain.

Examples of fatty acids are lauric acid ($C_{11}H_{23}COOH$), myristic acid ($C_{13}H_{27}COOH$), palmitic acid ($C_{15}H_{31}COOH$), stearic acid ($C_{17}H_{35}COOH$), oleic acid ($C_{17}H_{33}COOH$), linoleic acid ($C_{17}H_{31}COOH$), ricinoleic acid ($C_{17}H_{32}(OH)COOH$), linolenic acid ($CH_3CH_2CH=CHCH_2CH=CH_2CH=CH(CH_2)_7COOH$), arachinonic acid ($C_{19}H_{39}COOH$) or erucic acid ($C_{21}H_{43}COOH$).

In a variant of the invention, preference is given to fatty acids having an even number of carbons, i.e. preferably having 8, 10, 12, 14, 16, 18, 20 or 22 C atoms, particularly preferably having 12, 14, 16, 18 or 20 C atoms. However, it is also possible to employ synthetic fatty acids having an odd number of carbons.

In the fatty acid esters according to the invention, the group Y is preferably in the terminal position to the ester function. In fatty acids containing free OH groups in the side chain, these may likewise be replaced by Y, in particular by the group Y selected from the sub-group $CF_3$—$(CH_2)_9$—O—, where a stands for an integer selected from the range from 0 to 5 or

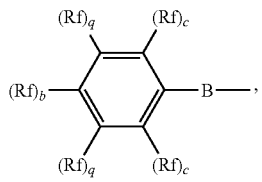

where

Rf stands for $CF_3$—$(CH_2)_r$—, $CF_3$—$(CH_2)_r$—O—, $CF_3$—$(CH_2)_r$—S—, $CF_3CF_2$—S—, $SF_5$—$(CH_2)_r$— or $[CF_3$—$(CH_2)_r]_2N$—, $[CF_3$—$(CH_2)_r]NH$— or $(CF_3)_2N$—$(CH_2)_r$—, B stands for O, NH, NR, $CH_2$, C(O)—O, C(O), S, $CH_2$—O, O—C(O), N—C(O), C(O)—N, O—C(O)—N, N—C(O)—N, O—$SO_2$ or $SO_2$—O, R stands for alkyl having 1 to 4 C atoms, b stands for 0 or 1 and c stands for 0 or 1, q stands for 0 or 1, where at least one radical from b and q stands for 1, and r stands for 0, 1, 2, 3, 4 or 5.

In a variant of the invention, the fatty acid is esterified using polyols, where the polyol radical in the fatty acid ester can be selected from an —O—$CH_2$—$(CHOH)_n$—$CH_2$—OH radical, where n=1, 2, 3, 4 or 5, a monosaccharide radical, a disaccharide radical or an oligosaccharide radical.

Examples of the polyols HO—$CH_2$—$(CHOH)_n$—$CH_2$—OH where n=1, 2, 3, 4 or 5 to be esterified are glycerin (or synonymously glycerol), D-threitol, L-threitol, erythrol, D-arabinitol, L-arabinitol, adonitol, xylitol, D-sorbitol, D-glucitol, D-mannitol, dulcitol, galactitol or also the tetrahydric branched alcohol pentaerythritol.

From this group of polyols, preference is given to the use of glycerol, erythrol, pentaerythritol, xylitol, sorbitol or mannitol, particularly preferably glycerol or sorbitol.

Examples of monosaccharides to be esterified are ribose, arabinose, xylose, lyxose, allose, altrose, glucose, mannose, gulose, idose, galactose, talose, ribulose, xylulose, psicose, fructose, sorbose or tagatose. This list contains both isomers, i.e. in each case the D or L forms.

From the group of the monosaccharides, preference is given to the use of glucose, galactose or fructose.

Examples of disaccharides to be esterified are saccharose (also known as sucrose), lactose, trehalose, maltose, cellobiose, gentiobiose or melibiose. This list contains both the α and the β forms.

From the group of the disaccharides, preference is given to the use of saccharose or lactose, particularly preferably saccharose.

Examples of polysaccharides to be esterified are, inter alia, also trisaccharides, such as raffinose, pseudooligosaccharides, such as acarbose, but also amylose, amylopectin, xanthan, insulin, chitin, pectins or cellulose.

In the fatty acid esters of polyols according to the invention, the esterification can in each case be adapted entirely to the number of hydroxyl groups in the polyol radical, or the esterification may be incomplete, i.e. the polyol radical contains both esterified and also free hydroxyl groups.

Depending on the application, as disclosed below, defined compounds, i.e. fatty acid esters having only one variant of the esterification of the polyol, or also mixtures of these fatty acid esters with different variants of the esterification of the polyol can be employed.

Preference is given to the use of the fatty acid esters of polyols according to the invention containing at least one fatty acid radical containing the group Y, as defined above. The composition of the mixtures can be controlled through the choice of the reagents and reaction conditions.

In a further preferred embodiment, particular preference is given to fatty acid esters of polyols in which the polyol radical is derived from glycerol, sorbitol or saccharose.

In the group Y, a preferably stands for 0, 1 or 2, particularly preferably for 0 or 2, very particularly preferably for 0, and r preferably stands for 0 to 3, in particular 0 to 1.

In a variant of the present invention, it is preferred for q in the group Y to stand for 0 and for at least one c and/or b each to stand for 1. It is particularly preferred for all c and b to stand for 1, i.e. the aromatic rings are substituted by fluorine groups in the o- and/or p-position, in particular in the o,p,o-position.

In a further variant of the invention, it is preferred for all q and b each to stand for 0 and for at least one c to stand for 1. It is particularly preferred for both c to stand for 1, i.e. the aromatic rings are substituted by fluorine groups in the opposition, in particular in the o,o-position.

In a further variant of the invention, it is preferred for all c and q each to stand for 0 and for b to stand for 1, i.e. the aromatic rings are substituted by fluorine groups in the p-position.

Of the fluorine groups as aryl substituents, which are also abbreviated to Rf below, preference is given to those in which r stands for 0, 1 or 2, where r preferably stands for 0. Particular preference is given in accordance with the invention to the groups Rf=CF$_3$—, CF$_3$—S—, CF$_3$CF$_2$—S—, SF$_5$— or (CF$_3$)$_2$N—.

In a preferred variant of the invention, the group Y, as defined above, which determines the modification of the fatty acid consists of CF$_3$—O—, CF$_3$—CF$_2$—S—, CF$_3$—S—, (CF$_3$)$_2$N— or

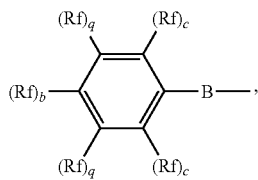

where
Rf stands for CF$_3$—(CH$_2$)$_r$—, CF$_3$—(CH$_2$)$_r$—O—, CF$_3$—(CH$_2$)$_r$—S—, CF$_3$CF$_2$—S—, SF$_5$—(CH$_2$)$_r$— or [CF$_3$—(CH$_2$)$_r$]$_2$N—, [CF$_3$—(CH$_2$)$_r$]NH— or (CF$_3$)$_2$N—(CH$_2$)$_r$—,
B stands for a single bond, O, NH, NR, CH$_2$, C(O)—O, C(O), S, CH$_2$—O, O—C(O), N—C(O), C(O)—N, O—C(O)—N, N—C(O)—N, O—SO$_2$ or SO$_2$—O,
R stands for alkyl having 1 to 4 C atoms,
b stands for 0 or 1 and c stands for 0 or 1,
q stands for 0 or 1, where at least one radical from b and q stands for 1, and
r stands for 0.

Rf preferably stands for CF$_3$—(CH$_2$)$_r$—, CF$_3$—(CH$_2$)$_r$—O—, CF$_3$—(CH$_2$)$_r$—S or [CF$_3$—(CH$_2$)$_r$]$_2$N—. A preferred variant of the invention encompasses fluorine groups, also abbreviated to Rf below, in which r stands for 0, 1, 2 or 3, in particular for 0, 1 or 2, where r preferably stands for 0.

In a particularly preferred embodiment of the present invention, Rf stands for CF$_3$—, CF$_3$—O—, CF$_3$—CH$_2$—CH$_2$—O—, CF$_3$—S—, CF$_3$CF$_2$—S—, SF$_5$—, CF$_3$—CH$_2$—CH$_2$—S—, (CF$_3$)$_2$—N— and (CF$_3$—CH$_2$—CH$_2$)$_2$—N—, in particular for CF$_3$—, CF$_3$—O—, CF$_3$—S— and (CF$_3$)$_2$—N—.

A further preferred variant of the invention encompasses the groups Rf which are equal to CF$_3$—, CF$_3$—S—, CF$_3$CF$_2$—S—, SF$_5$— or (CF$_3$)$_2$N—.

Particularly preferred groups B are O, S, CH$_2$O, CH$_2$, C(O) and OC(O). In particular, B equal to O and OC(O) are preferred.

A particularly preferred variant of the invention encompasses the groups Y which are equal to CF$_3$—Ar—O, CF$_3$—O—Ar—O, CF$_3$—CH$_2$—CH$_2$—O—Ar—O, CF$_3$—S—Ar—O, CF$_3$CF$_2$—S—Ar—O, SF$_5$—Ar—O, CF$_3$—CH$_2$—CH$_2$—S—Ar—O, (CF$_3$)$_2$—N—Ar—O, (CF$_3$—CH$_2$—(CH$_2$)$_2$—N—Ar—O, CF$_3$—Ar—OC(O), CF$_3$—O—Ar—OC(O), CF$_3$—CH$_2$—CH$_2$—O—Ar—OC(O), CF$_3$—S—Ar—OC(O), CF$_3$CF$_2$—S—Ar—OC(O), SF$_5$—Ar—OC(O), CF$_3$—CH$_2$—CH$_2$—S—Ar—OC(O), (CF$_3$)$_2$—N—Ar—OC(O) and (CF$_3$—CH$_2$—(CH$_2$)$_2$—N—Ar—OC(O), in particular equal to CF$_3$—Ar—O, CF$_3$—O—Ar—O, CF$_3$—S—Ar—O, (CF$_3$)$_2$—N—Ar—O, CF$_3$—Ar—OC(O), CF$_3$—O—Ar—OC(O), CF$_3$—S—Ar—OC(O) and (CF$_3$)$_2$—N—Ar—OC(O).

A particularly preferred variant of the invention encompasses Y equal to CF$_3$—Ar—O and CF$_3$—Ar—OC(O).

In a variant of the present invention, it is preferred for q to stand for 0 and for at least one c and/or b each to stand for 1.

It is particularly preferred for all c and b to stand for 1, i.e. the aromatic rings are substituted by fluorine groups in the o,p, o-position.

In a further variant of the invention, it is preferred for all q and b each to stand for 0 and for at least one c to stand for 1. It is particularly preferred for both c to stand for 1, i.e. the aromatic rings are substituted by fluorine groups in the o,o-position.

In a further variant of the invention, it is preferred for all c and q each to stand for 0 and for b to stand for 1, i.e. the aromatic rings are substituted by fluorine groups in the p-position.

Particular preference is given to the use of compounds which have a combination of the variables in their preferred or particularly preferred ranges.

Further preferred combinations are disclosed in the claims.

A further preferred embodiment encompasses fatty acid esters of sorbitol, which can be reproduced by the formula IA

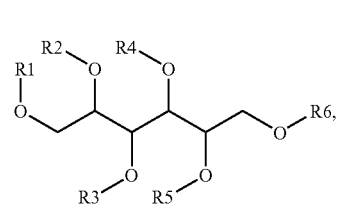

where
R1 to R6 correspond to a fatty acid radical containing the group Y, as defined above, or H, where the radicals R1 to R6 cannot all be equal to H.

A further preferred embodiment encompasses fatty acid esters of saccharose, which can be reproduced by the formula IB

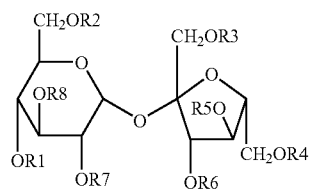

where
R1 to R8 correspond to a fatty acid radical containing the group Y, as defined above, or H, where the radicals R1 to R8 cannot all be equal to H.

The fatty acid esters of polyols according to the invention can be prepared by methods known per se to the person skilled in the art from the literature. The reaction conditions for esterifications are standard prior art, and the selection of suitable reaction conditions is standard to the person skilled in the art of synthesis. The esterification with the free acid is preferably carried out, for example, with acid catalysis, but can also be carried out enzymatically. Another variant is the reaction of fatty acid chlorides under mild conditions in the presence of pyridine.

Fatty acid esters of carbohydrates, i.e. mono-, di- or polysaccharides, are prepared, for example, via the fatty acid methyl ester with alkali catalysis, where the methanol formed is distilled off, where the temperature during this reaction should remain below 100° C. Literature in this respect is Ullmann's Encyclopaedia of Industrial Chemistry Release 2006, 7th Edition, article on "Surfactants", author: Kurt Kosswig, DOI: 10.1002/14356007.a25_747.

The invention therefore furthermore relates to a process for the preparation of fatty acid esters of polyols according to the invention, characterised in that a fatty acid containing the group Y, as defined above, or a derivative of this fatty acid is esterified using a polyol.

Derivatives of this fatty acid are, as described above, fatty acid chlorides or lower esters of fatty acids, for example the methyl esters.

Examples of the synthesis of the modified saturated fatty acids are revealed by the following scheme. The synthesis of the modified unsaturated fatty acids is correspondingly analogous.

1. For the group Y=OCF$_3$ and for saturated fatty acids CH$_3$—(CH$_2$)$_{s-1}$—COOH, whose alkylene units are represented by (CH$_2$)$_s$ in the schemes, where s can be equal to 4 to 25:

Variant A:

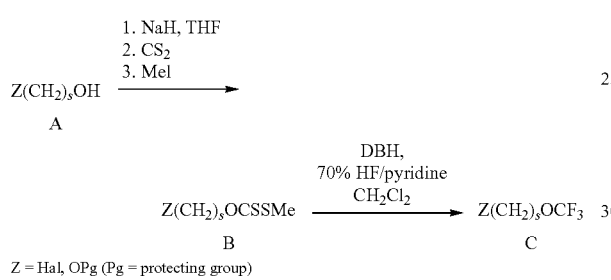

Z = Hal, OPg (Pg = protecting group)

The aliphatic OCF$_3$ group can be obtained, for example, from a precursor A=Z(CH$_2$)$_s$—OH via the fluorodesulfuration of xanthogenates (K. Kanie, Y. Tanaka, K. Suzuki, M. Kuroboshi, T. Hiyama, Bull. Chem. Soc. Jpn. 2000, 73, 471-484; P. Kirsch, Modern Fluoroorganic Chemistry: Synthesis, Reactivity, Applications, Wiley-VCH, Weinheim, 2004, pp. 67 ff., pp. 144 ff.). The corresponding disclosure of the said method in the cited references thus expressly also belongs to the disclosure content of the present application.

The derivatisation of the deprotected alcohol to give the acid is subsequently carried out by oxidation.

Derivatisation for Z = OPg (e.g. OBn = O-benzyl):

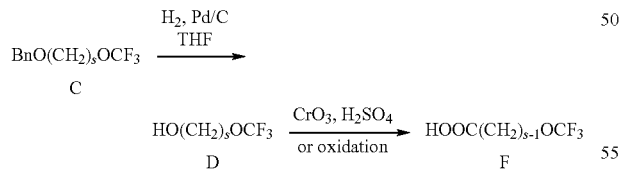

Alternatively, the modified fatty acid can be prepared by variant B:

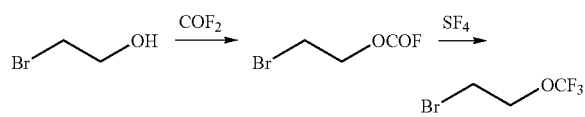

2-Bromoethanol is converted into the fluoroformate, and the carbonyl group is subsequently transformed into the OCF$_3$ ether using SF$_4$.

LITERATURE

1. Aldrich, P. E.; Sheppard, William A. J. Org. Chem. 1964, 29, 11-15
2. Sheppard, William A. et al. J. Org. Chem. 1964, 29, 1-11
3. Yagupol'skii, L. M.; Alekseenko, A. N.; Il'chenko, A. Y Ukrainskii Khimicheskii Zhurnal 1978, 44, 1057-1059

The fatty acid is now obtained by: 1. Williamson ether synthesis, 2. subsequent hydrogenolytic debenzylation, and 3. subsequent oxidation using stoichiometric amounts of sodium periodate and catalytic amounts of ruthenium chloride.

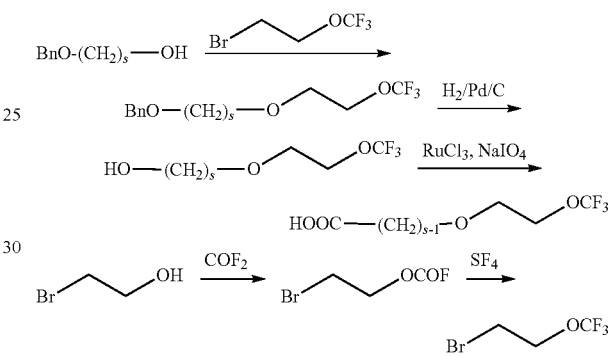

2. For the group Y=CF$_3$—(CH$_2$)$_a$—O—, where a=1 to 5, and for saturated fatty acids, whose alkylene units are represented by (CH$_2$)$_s$ in the schemes, where s can be equal to 4 to 25: The CF$_3$—(CH$_2$)$_a$—O— group is introduced by reaction of CF$_3$—(CH$_2$)$_a$—OH, where a=1, 2, 3, 4 or 5, with a primary hydroxy ester via a Mitsunobu reaction (Mitsunobu, O. Synthesis, 1981, 1) to give the corresponding fatty acid esters.

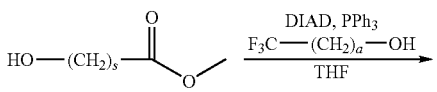

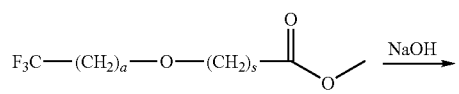

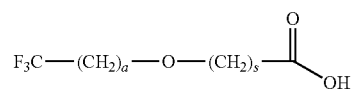

DIAD = diisopropyl azodicarboxylate

Alternatively, the modified fatty acid can also be prepared by dietherification of the alcohol CF$_3$—(CH$_2$)$_a$—OH, where a=1 to 5, onto a corresponding brominated alkene and subsequent ozonolysis with oxidative work-up.

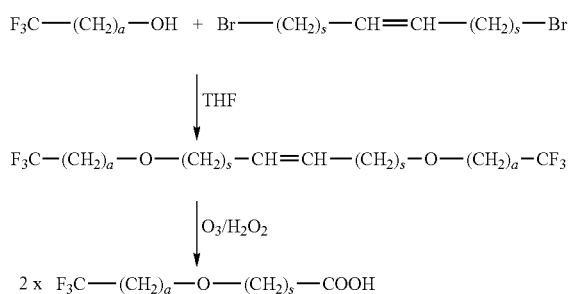

3. For the group Y=SF$_5$ and for saturated fatty acids, whose alkylene units are represented by (CH$_2$)$_s$ in the schemes, where s can be equal to 4 to 25: The aliphatic SF$_5$ group can be introduced, for example, at terminal double bonds via the free-radical addition reaction of SF$_5$C$_1$ or SF$_5$Br. A dehydrohalogenation or a hydrogenation, for example, can subsequently optionally be carried out. The first two of these reaction steps are described in the literature (R. Winter, P. G. Nixon, G. L. Gard, D. H. Radford, N. R. Holcomb, D. W. Grainger, J. Fluorine Chem. 2001, 107, 23-30), as are catalytic hydrogenations in the presence of an SF$_5$ function (P. Kirsch, M. Bremer, M. Heckmeier, K. Tarumi, Angew, Chem. 1999, 111, 2174-2178; Angew. Chem. Int. Ed. Engl. 1999, 38, 1989-1992). The corresponding disclosure of the said method in the cited references thus expressly also belongs to the disclosure content of the present application. Examples are revealed by the following scheme:

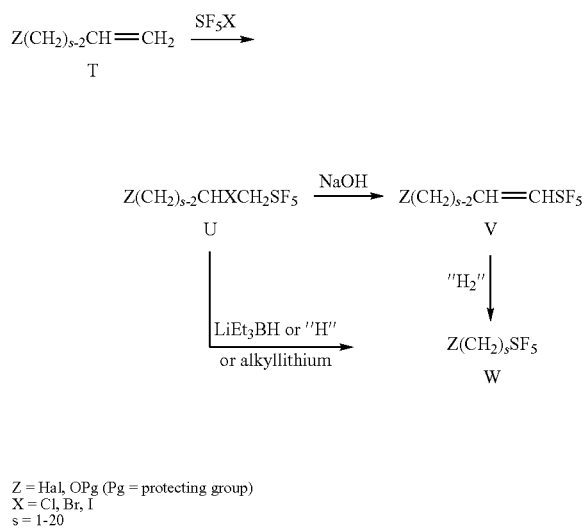

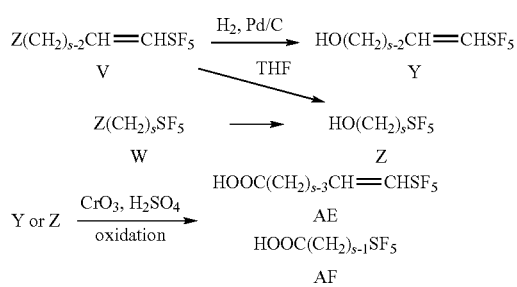

An alternative synthesis of the SF$_5$-modified fatty acid is the addition of SF$_5$Cl onto a terminal double bond of a fatty acid ester, for example a methyl ester, elimination of HCl and subsequent ester cleavage.

4. For the group Y=CF$_3$—S or CF$_3$—CF$_2$—S and for saturated fatty acids, whose alkylene units are represented by (CH$_2$)$_s$ in the schemes, where s can be equal to 4 to 25:

Acids or acid derivatives containing a terminal thiol group are commercially available or can be prepared by methods known to the person skilled in the art. Conversion into the desired CF$_3$—S or CF$_3$—CF$_2$—S group is carried out, for example, in accordance with the following scheme and in accordance with Anselmi, E. et al. J. Fluorine Chem. 2000, 105, 1, 41-44 or can optionally be prepared by: Se (trifluoromethyl)dibenzoselenophenium triflate (Umemoto's reagent): T. Umemoto et al. J. Am. Chem. Soc. 1993, 115, 2156-2164.

Or via: N. V. Ignatiev, Ukr. Khim. Zh. 2001, No. 10, pp. 98-102.

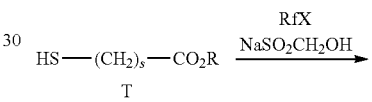

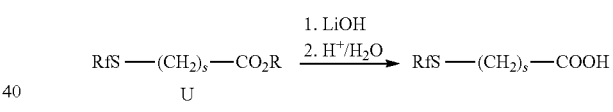

5. For the group Y=(CF$_3$)$_2$N— and for saturated fatty acids, whose alkylene units are represented by (CH$_2$)$_s$ in the schemes, where s can be equal to 4 to 25:

The aliphatic (CF$_3$)$_2$N— group is introduced into the fatty acids firstly by reaction of corresponding tetramethylammonium salts with halides which have a corresponding number of C atoms for the desired fatty acid and a terminal double bond, in accordance with the scheme shown. The respective tetramethylammonium salts can be obtained analogously to the description of EP 1081129. The corresponding disclosure of the said method in the cited references thus expressly also belongs to the disclosure content of the present application.

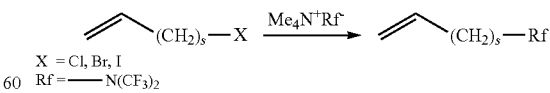

The terminal double bond can be converted into the carboxyl function by methods known to the person skilled in the art. Examples are revealed by the following scheme, where Rf in the following scheme can be N(CF$_3$)$_2$, but also SCF$_3$ or SC$_2$F$_5$:

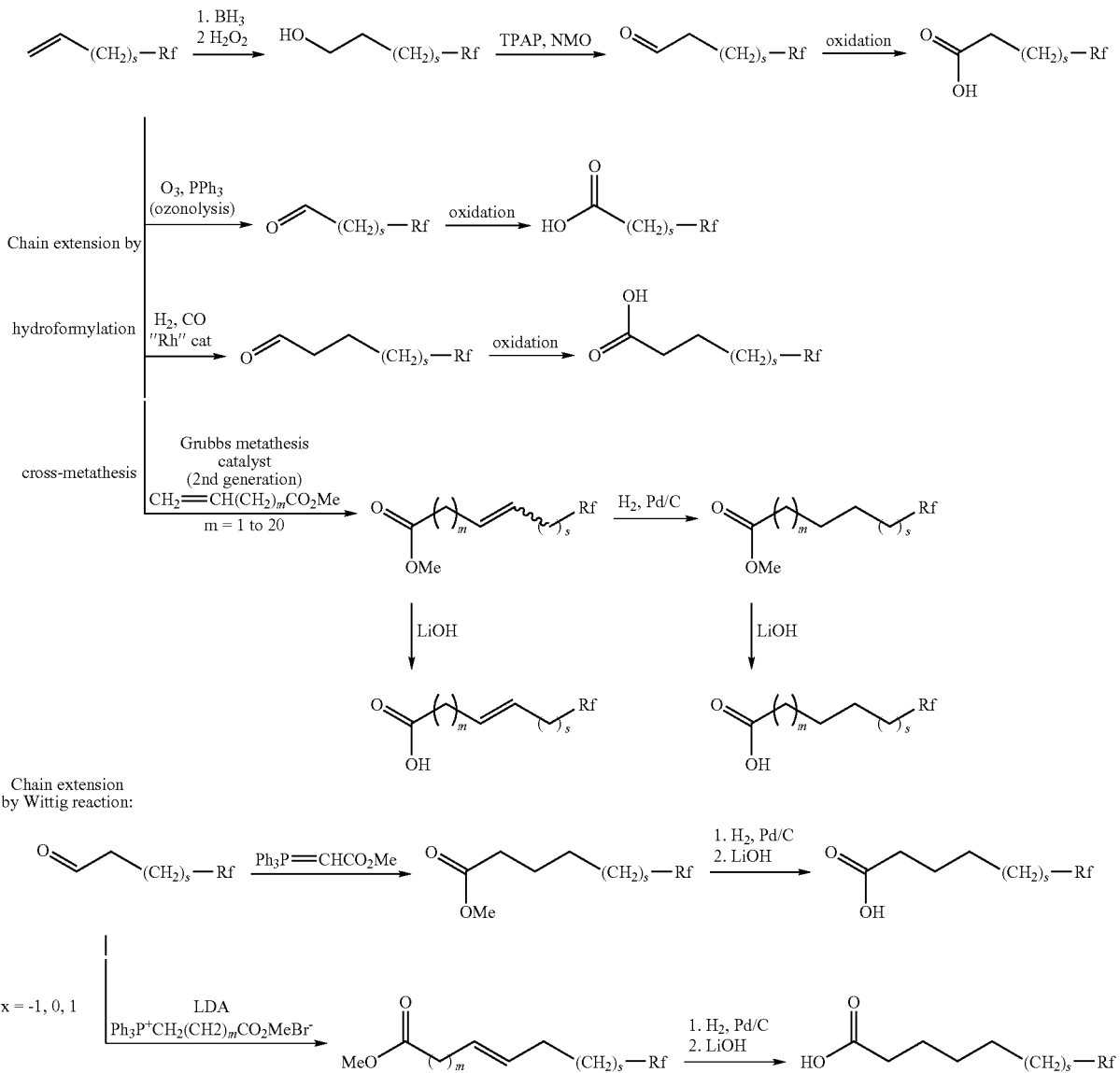

The amine unit $[CF_3-(CH_2)_a]_2N-$, where a stands for an integer selected from the range from 1 to 5, can be introduced with the aid of the Gabriel synthesis (Organikum: Organisch-Chemisches Grundpraktikum [Basic Practical Organic Chemistry], 16th Edn., VEB Deutscher Verlag der Wissenschaften, Berlin, 1986), followed by liberation of the primary amine by reaction with hydrazine. Subsequent alkylation of this amine using $CF_3(CH_2)Hal$ and debenzylation gives the tertiary amino alcohol as key unit.

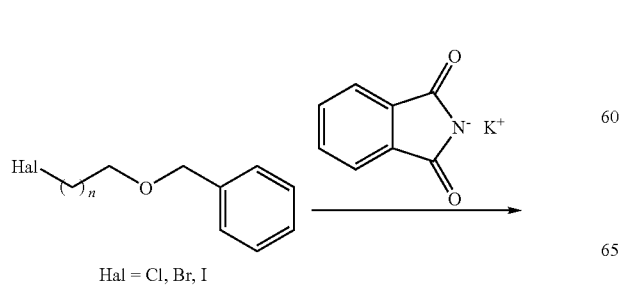

-continued

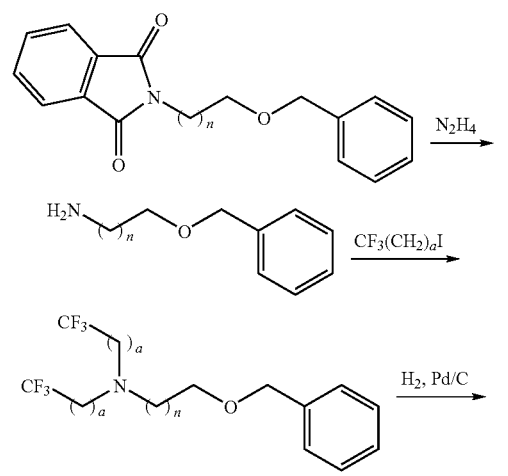

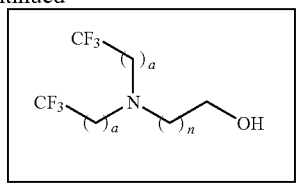

Subsequent oxidation by, for example, $CrO_3/H_2SO_4$ results in the modified acid.

6. For the group $Y=CF_3—(CH_2)_a—S—$, where a=1 to 5, and for saturated fatty acids, whose alkylene units are represented by $(CH_2)_s$ in the schemes, where s can be equal to 4 to 25;

The $CF_3—(CH_2)_a—S—$ group is introduced, for example, by reaction of $CF_3—(CH_2)_a—OH$, where a=1, 2, 3, 4 or 5, with a fatty acid ester containing a terminal thiol group via a Mitsunobu reaction (Mitsunobu, O. Synthesis, 1981, 1) to give the corresponding fatty acid esters, where the alcohols of the formula $CF_3—(CH_2)_a—OH$ are commercially available or are readily accessible from commercial substances.

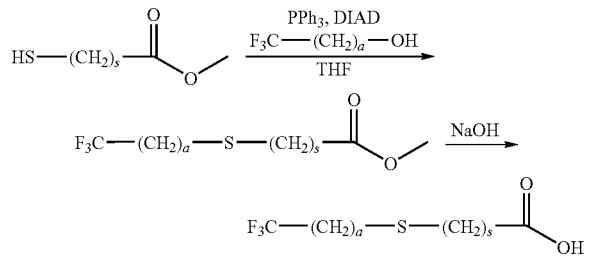

Analogously to Examples 5a-c, $CF_3S—$ or $CF_3CF_2S—$ or $CF_3(CH)_a—$ end groups can also be introduced instead of $(CF_3)_2N—$ end groups. In the case of sulfur-containing compounds, Pt or Ru catalysts are employed instead of Pd catalysts.

7. For the group $Y=CF_3NH—$:

The end group $CF_3NH—$ in compounds $CF_3NH—R$ can be introduced by methods known from the literature by reaction of corresponding compounds $Cl_2C=N—R$ with an excess of HF (corresponding syntheses are described, for example, in Petrow et al., Zh. Obshch. Khim. 29 (1959) 2169-2172). Alternatively, it is also possible to react trifluoromethyl isocyanate with an alcohol to give a compound $CF_3—NHC(=O)—O—R$ (as described by Knunyants et al. Mendeleev chem. J. 22 (1977) 15-105 or Motornyi et al., Zh. Obshch. Khim. 29 (1959) 2157-2122). The corresponding starting materials are each obtainable by methods known from the literature, and the radicals R of the products can be chemically modified by established methods.

8. For the group Y=

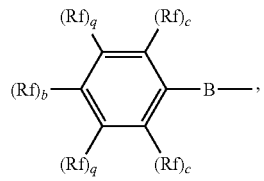

where

Rf stands for $CF_3—(CH_2)_r—$, $CF_3—(CH_2)_r—O—$, $CF_3—(CH_2)_r—S—$, $CF_3CF_2—S—$, $SF_5—(CH_2)_r—$ or $[CF_3—(CH_2)_r]_2N—$, $[CF_3—(CH_2)_r]NH—$ or $(CF_3)_2N—(CH_2)_r—$, B stands for a single bond, O, NH, NR, $CH_2$, C(O)—O, C(O), S, $CH_2$—O, O—C(O), N—C(O), C(O)—N, O—C(O)—N, N—C(O)—N, O—$SO_2$ or $SO_2$—O, R stands for alkyl having 1 to 4 C atoms, b stands for 0 or 1 and c stands for 0 or 1, q stands for 0 or 1, where at least one radical from b and q stands for 1, and r stands for 0, 1, 2, 3, 4 or 6, and for saturated fatty acids, where the alkylene units are represented by $(CH_2)_s$ in the schemes, where s can be equal to 4 to 25:

This aromatic group is introduced into the fatty acids in accordance with the scheme indicated. In some cases, the respective Rf-substituted aromatic compounds are commercially available. Otherwise, synthetic methods are also indicated in each case. The corresponding disclosure of the said method in the cited references thus expressly also belongs to the disclosure content of the present application.

The group Rf stands for $CF_3—(CH_2)_r—$, $CF_3—(CH_2)_r—O—$, $CF_3—(CH_2)_r—S—$, $CF_3CF_2—S—$, $SF_5—(CH_2)_r—$, $[CF_3—(CH_2)_r]_2N—$, $[CF_3—(CH_2)_r]NH—$ or $(CF_3)_2N—(CH_2)_r—$, with indices as described above, and can be introduced by means of substitution reactions on aromatic compounds. If Rf is used in the following schemes, the definition given here applies, unless indicated otherwise.

The bonding of a spacer to aryl-Rf or further links via various functionalities are shown in Schemes I to VIII:

I. Etherification by Mitsunobu Reaction:

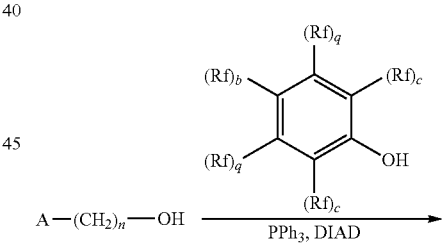

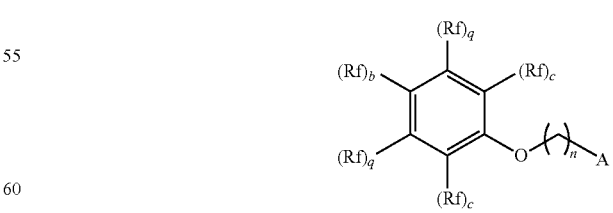

A = —$CO_2R$, where R = Me, Et
q = 0 and/or 1
b = 0 and/or 1
c = 0 and/or 1
n = 4-25

II. Linking via Thioether or Sulfone Unit

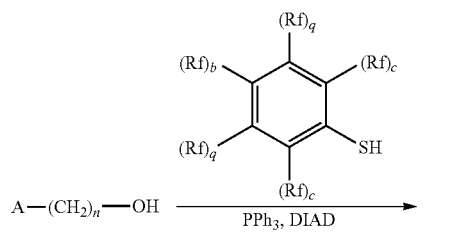

A = —CO$_2$R, where R = Me, Et
q = 0 and/or 1
b = 0 and/or 1
c = 0 and/or 1
n = 4-25

III. Amine Formation

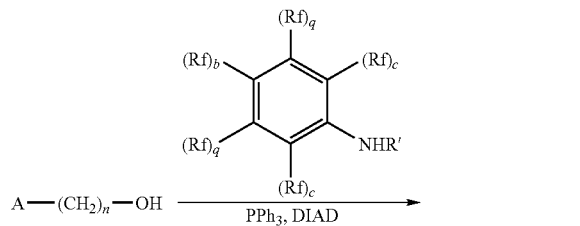

A = —CO$_2$R, where R = Me, Et
R' = H or alkyl having 1 to 4 C atoms
q = 0 and/or 1
b = 0 and/or 1
c = 0 and/or 1
n = 4-25

IV. Esterification or Amide Formation

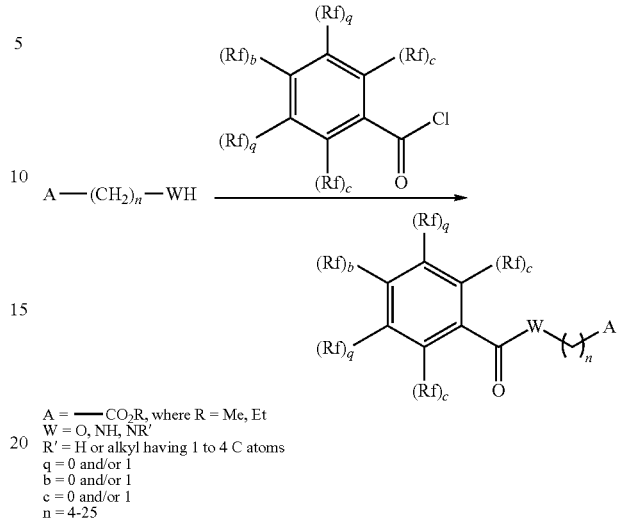

A = —CO$_2$R, where R = Me, Et
W = O, NH, NR'
R' = H or alkyl having 1 to 4 C atoms
q = 0 and/or 1
b = 0 and/or 1
c = 0 and/or 1
n = 4-25

A = —CO$_2$R, where R = Me, Et
W = O, NH, NR
q = 0 and/or 1
b = 0 and/or 1
c = 0 and/or 1
n = 4-25

V. Linking via Sulfonic Acid Esters and Amides

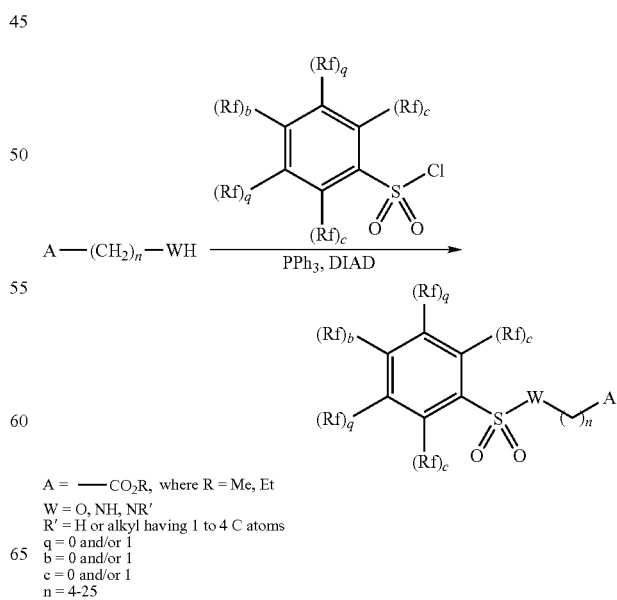

A = —CO$_2$R, where R = Me, Et
W = O, NH, NR'
R' = H or alkyl having 1 to 4 C atoms
q = 0 and/or 1
b = 0 and/or 1
c = 0 and/or 1
n = 4-25

The arylsulfonyl chloride is obtained from the corresponding aromatic compound by reaction with ClSO$_3$H.

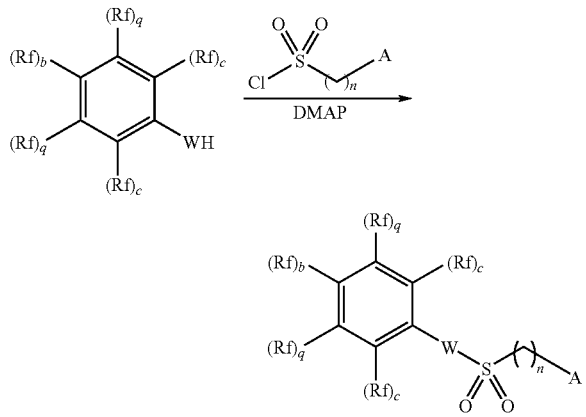

A = —CO$_2$R, where R = Me, Et
W = O, NH, NR'
R' = H or alkyl having 1 to 4 C atoms
q = 0 and/or 1
b = 0 and/or 1
c = 0 and/or 1
n = 4-25

VI. Linking via Keto Function

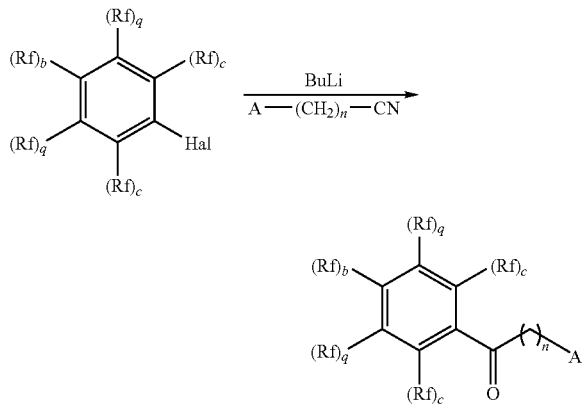

A = —CO$_2$R, where R = Me, Et
W = O, NH, NR'
Hal = Cl, Br, I
q = 0 and/or 1
b = 0 and/or 1
c = 0 and/or 1
n = 4-25

VII. Linking via Isocyanates or Isothiocyanates

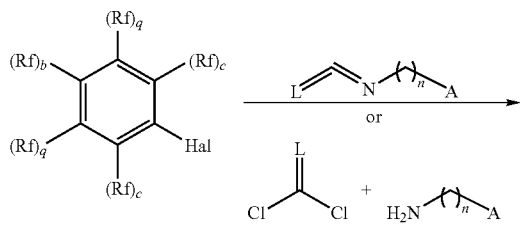

A = —CO$_2$R, where R = Me, Et
W = O, NH, NR'
L = O, S
q = 0 and/or 1
b = 0 and/or 1
c = 0 and/or 1
n = 4-25

VIII. Linking via Heck Reaction

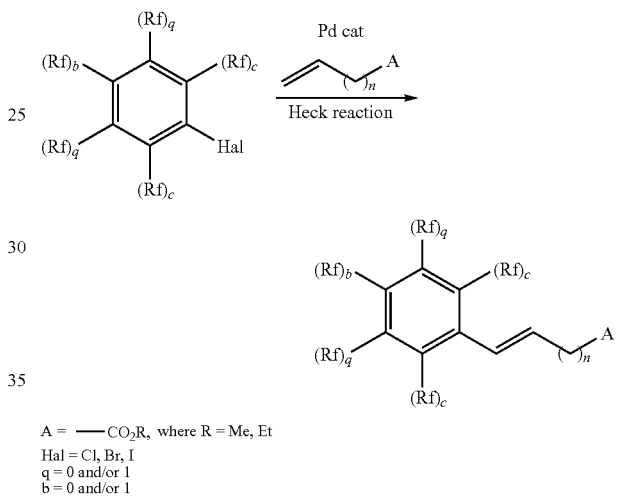

A = —CO$_2$R, where R = Me, Et
Hal = Cl, Br, I
q = 0 and/or 1
b = 0 and/or 1
c = 0 and/or 1
n = 4-25

The aryl units with the said Rf substituents can be synthesised by the following reactions:

For CF$_3$ substitution: the CF$_3$ groups can be obtained by reaction of aromatic carboxylic acids with HF and SF$_4$ under superatmospheric pressure and elevated temperature, as indicated in the following scheme:

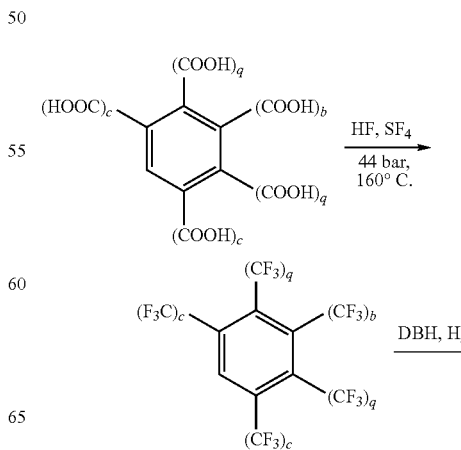

19

-continued

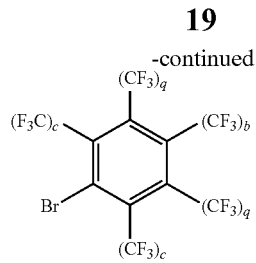

1. BuLi
2. (Me₃O)₃B
3. H₂O₂
→

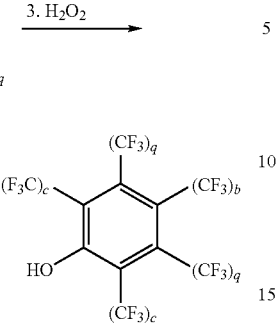

Number of substituents:
c: ortho-position (0 or at least 1)
q: meta-position (0 or at least 1)
b: para-position (0 or at least 1)
DBH = 1,3-dibromo-5,5-dimethylhydantoin

20

Compounds of the Formula

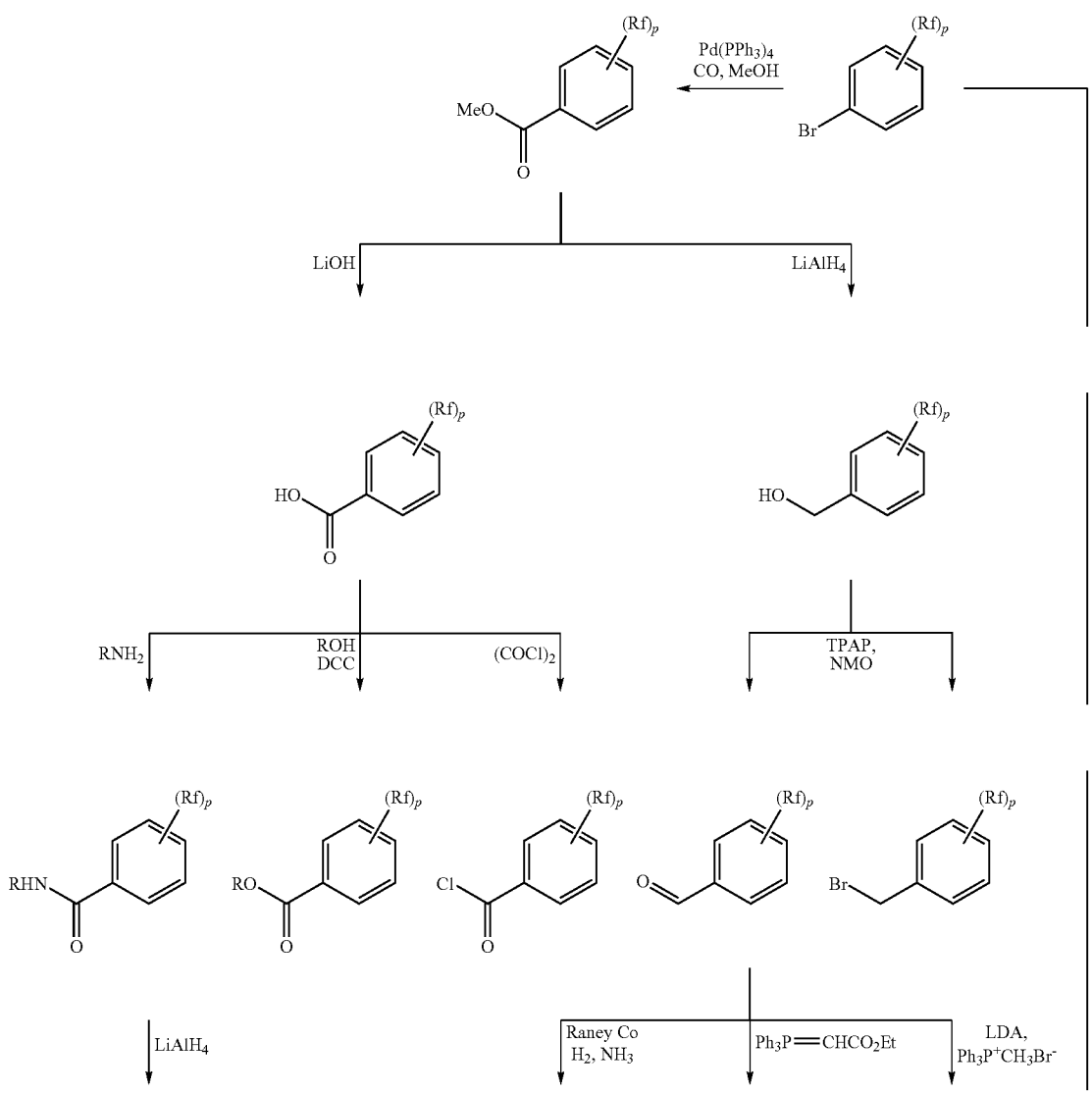

where G=—CO₂H, CH₂NH₂, —CH₂OH, —CHO, —COCl,
—CH₂Br, —CH₂CO₂H, —CH═CH₂, —CH═CHCO₂H,
—C≡CCH₂OH,
are commercially available.

Derivatisation for Aromatic Systems Containing Fluorinated CF₃ Groups:

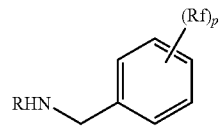 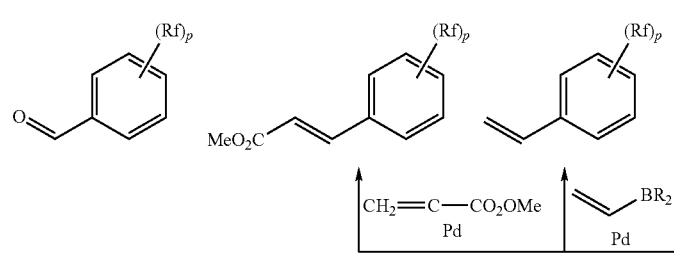
[Number p of Rf substituents (p = 1 to 5) and position on the aromatic ring flexible]
Derivatisation for Aromatic Systems Containing 3 Fluorinated $CF_3$ Groups:

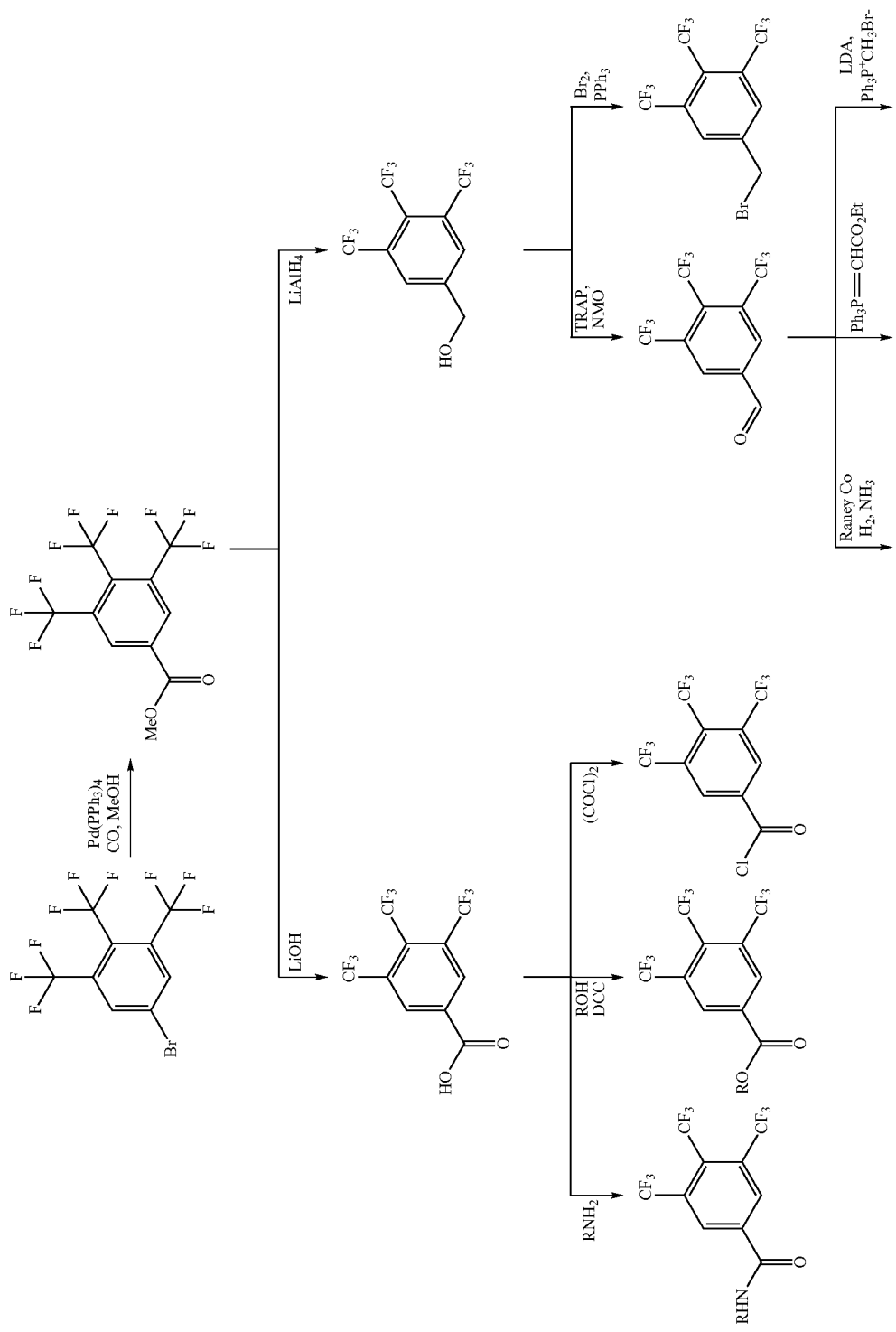

-continued
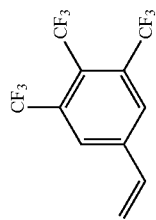
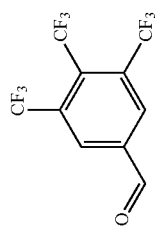
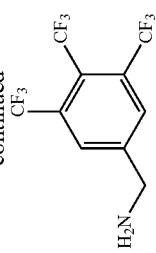

DCC: dicyclohexylcarbodiimide
TPAP: tetra-n-propylammonium perruthenate
THP: tetrahydropyranyl The following applies for SF$_5$:

The modification of commercial p-nitropentafluorosulfuranyl compounds can be carried out as described in P. Kirsch et al. Angewandte Chemie 1999, 111, 2174-2178.

The corresponding disclosure of the said methods in the cited references thus expressly also belongs to the disclosure content of the present application.

The following applies for F$_3$CS— or F$_5$C$_2$S—:

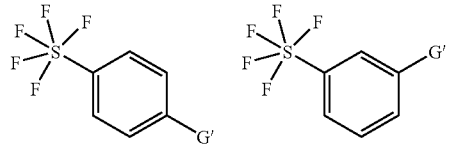

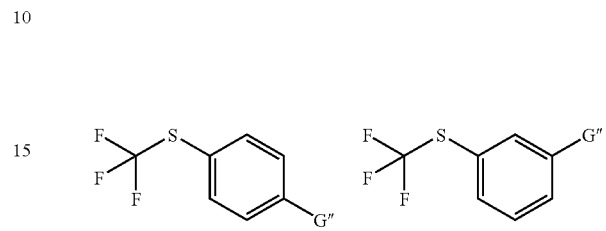

Commercial reagents are:
G'=—OH, —Br, —NH$_2$, —NO$_2$, —CHO, —CO$_2$H

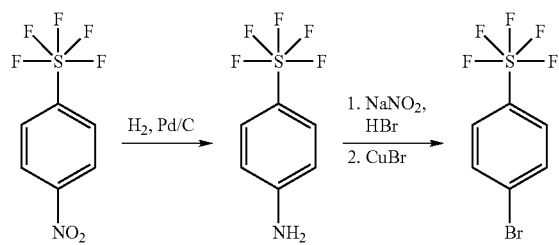

Commercial reagents are:
G''=—OH, —Br, —Cl, —NH$_2$, —NO$_2$, —N=C=O, —CHO, —CO$_2$H, —CN, —CH$_2$OH, —CH$_2$Br The m,m-bispentafluorosulfuranyl compounds are accessible as described in W. A. Sheppard J. Am. Chem. Soc. 1962, 84, 3064-3072 or U.S. Pat. No. 3,073,861 or U.S. Pat. No. 3,135,736:

Aromatic trifluoromethyl thioethers and pentafluoroethyl thioethers are accessible by substitution of iodoaromatic compounds or etherification of thiophenols, as indicated in the following scheme:

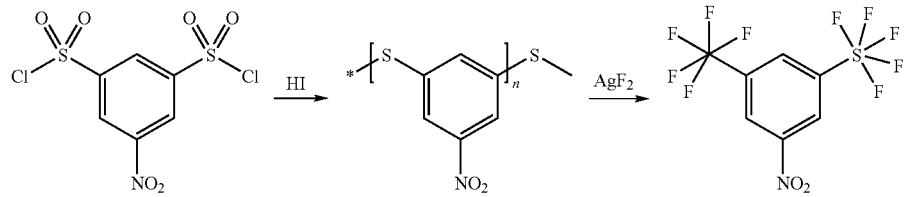

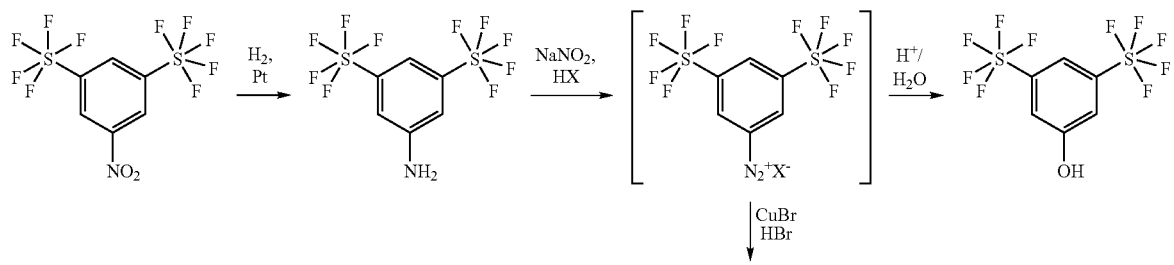

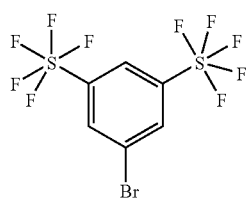

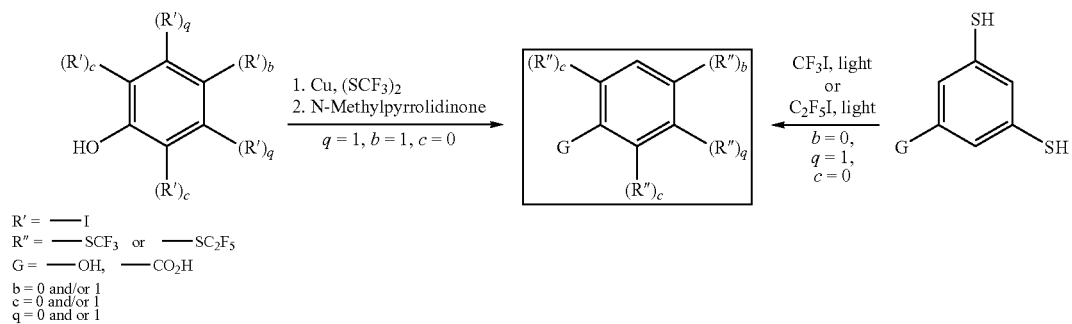

R' = —I
R" = —SCF₃ or —SC₂F₅
G = —OH, —CO₂H
b = 0 and/or 1
c = 0 and/or 1
q = 0 and/or 1 or

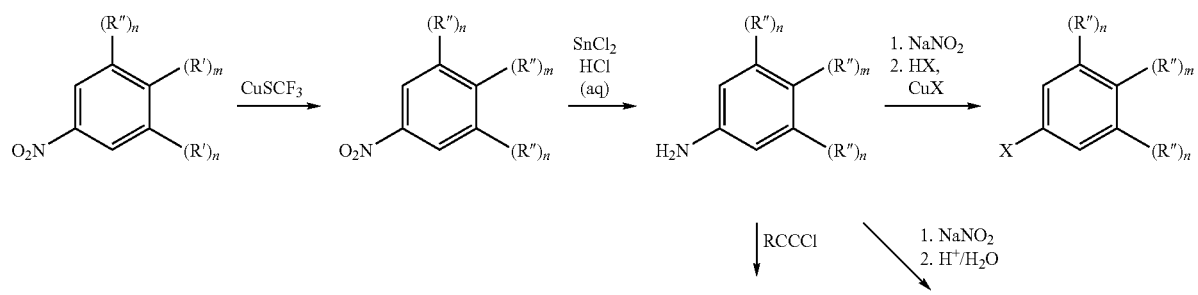

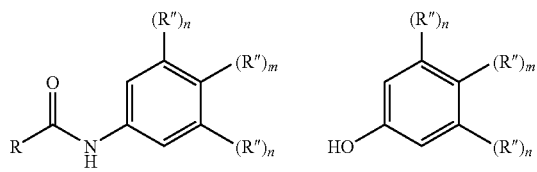

The following applies for F₃CO:

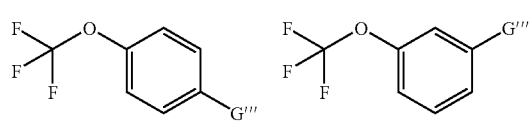

Commercial reagents or substances which are readily accessible therefrom are:

G'''= —OH, —I, —Br, —Cl, —NH₂, —SH, —B(OH)₂, —CHO, —CO₂H, —CO₂Me, —CONH₂, —CN, —CH₂OH, —CH₂Br, —CH₂CN.

Trifluoromethoxyaromatic compounds can be obtained by reaction of phenols with carbon tetrachloride and hydrogen fluoride,

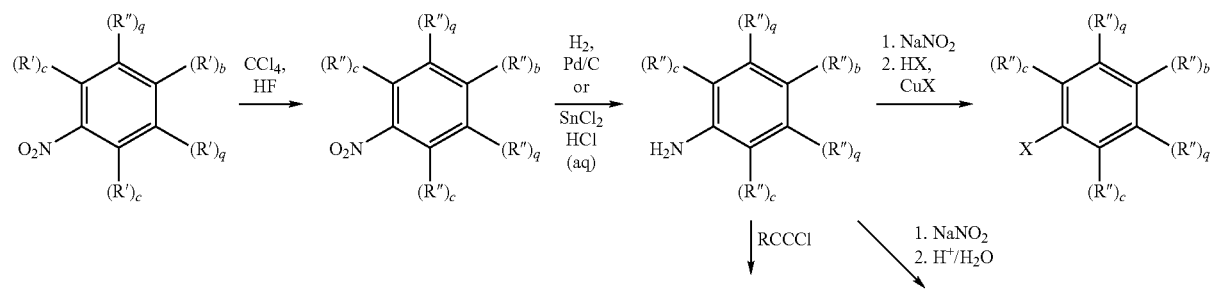

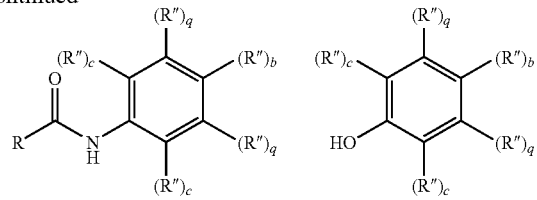

R = subst./unsubst. aryl, alkyl
R' = —I
R" = —OCF$_3$
X = Cl, Br
c = 0 and/or 1
q = 0 and/or 1
b = 0 and/or 1

SPECIFIC EXAMPLE

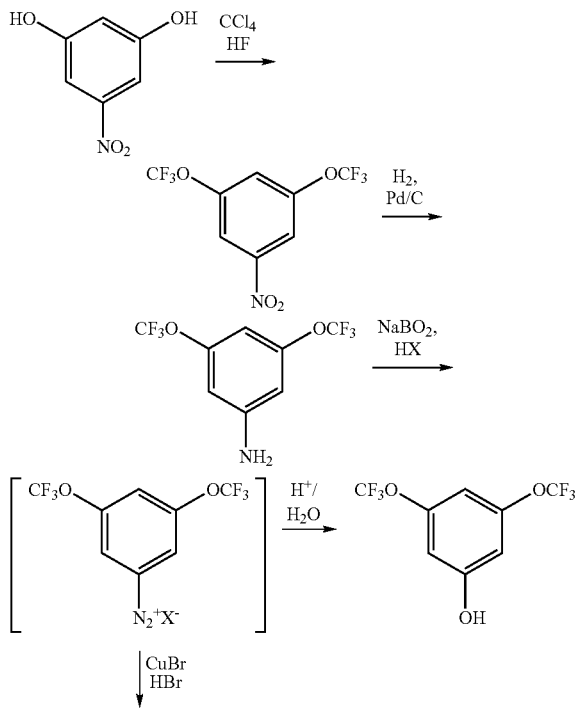

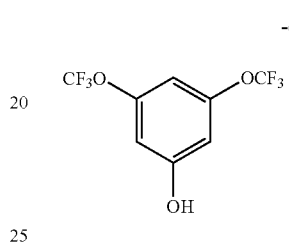

The starting material nitroresorcinol can be prepared in accordance with the following literature:

Ref. 1 Funke; Krucker; BSCFAS; Bull. Soc. Chim. Fr.; 1953; 744, 746.

Ref. 1 Grosheintz; Fischer; JACSAT; J. Am. Chem. Soc.; 70; 1948; 1476, 1478.

The following applies for [CF$_3$—(CH$_2$)$_a$]$_2$N—,

The amine unit [CF$_3$—(CH$_2$)$_a$]$_2$N—, where a stands for an integer selected from the range from 0 to 5, can be introduced with the aid of the Gabriel synthesis (Organikum: Organisch-Chemisches Grundpraktikum [Basic Practical Organic Chemistry], 16th Edn., VEB Deutscher Verlag der Wissenschaften, Berlin, 1986), followed by liberation of the primary amine by reaction with hydrazine. Subsequent alkylation of this amine using CF$_3$(CH$_2$)$_x$Hal and debenzylation gives the tertiary amino alcohol as key unit.

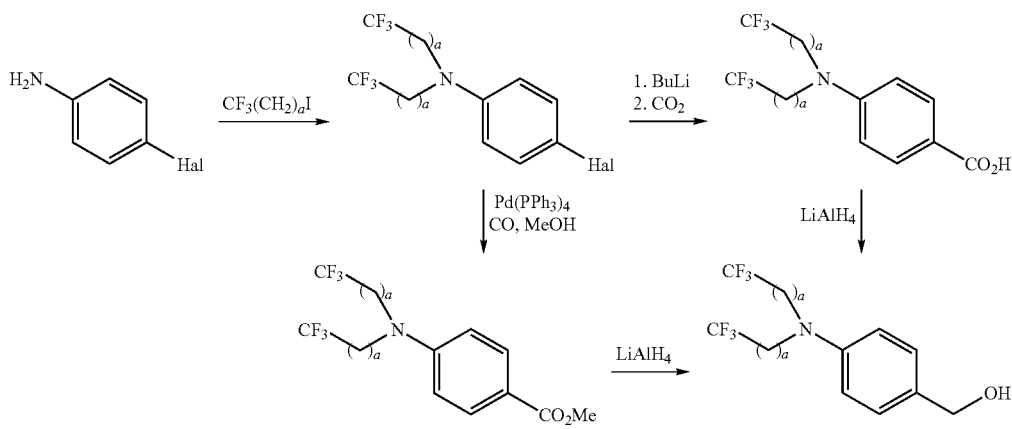

The following applies for $(CF_3)_2N$—:

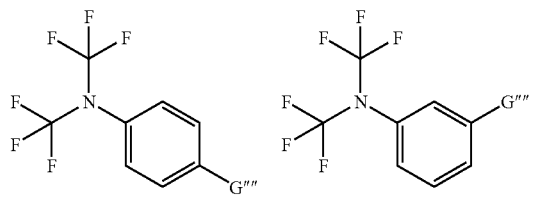

Commercial reagents or substances which are readily accessible therefrom are:
G''''=—OH, —I, —Br, —Cl, —NH$_2$, —NHAc, —CHO, —CO$_2$H, —CO$_2$Me, —CONH$_2$, —CN, —CH$_2$OH, —CH$_2$Br, —CH$_2$CN.

$(CF_3)_2N$ substituents can be obtained as described by F. S. Fawcett; J. Am. Chem. Soc. 84 (No. 22) (1962) 4275-4285 starting from isocyanates by reaction with fluorophosgene and subsequent fluorination using SF$_4$/HF or starting from isothiocyanates by reaction with mercury difluoride and subsequent reaction with fluorophosgene, and subsequent fluorination using SF$_4$/HF:

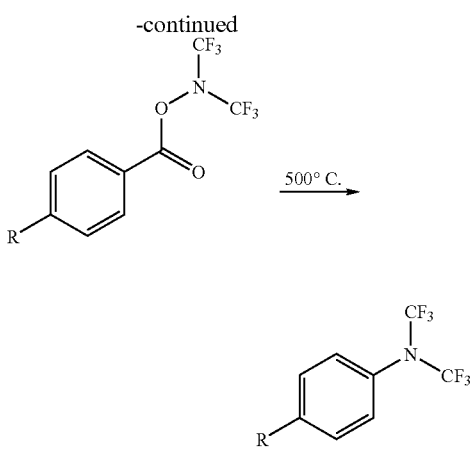

R preferably stands for spacer -X
or —OH or —Br or —Cl or —I
or —COOH

The following applies for CF$_3$NH—:

The end group CF$_3$NH— in compounds CF$_3$NH—R can be introduced by methods known from the literature by reaction of corresponding compounds Cl$_2$C=N—R with an excess of HF (corresponding syntheses are described, for example, in Petrow et al., Zh. Obshch. Khim. 29 (1959) 2169-2173 or E. Kuhle, Angew. Chem. 89 (No. 11) (1977), 797-804). Alternatively, trifluoromethyl isocyanate can also be reacted with an alcohol to give a compound CF$_3$—NHC(=O)—O—R (as described by Knunyants et al. Mendeleev chem. J. 22 (1977) 15-105 or Motornyi et al., Zh. Obshch. Khim. 29 (1959) 2157-2122). The corresponding starting materials are each obtainable by methods known from the literature, or compounds of the Cl$_2$C=N—R type can be obtained by reactions of compounds R—NH—CHO with chlorine and SOCl$_2$, and the radicals R of the products can be chemically modified by established methods.

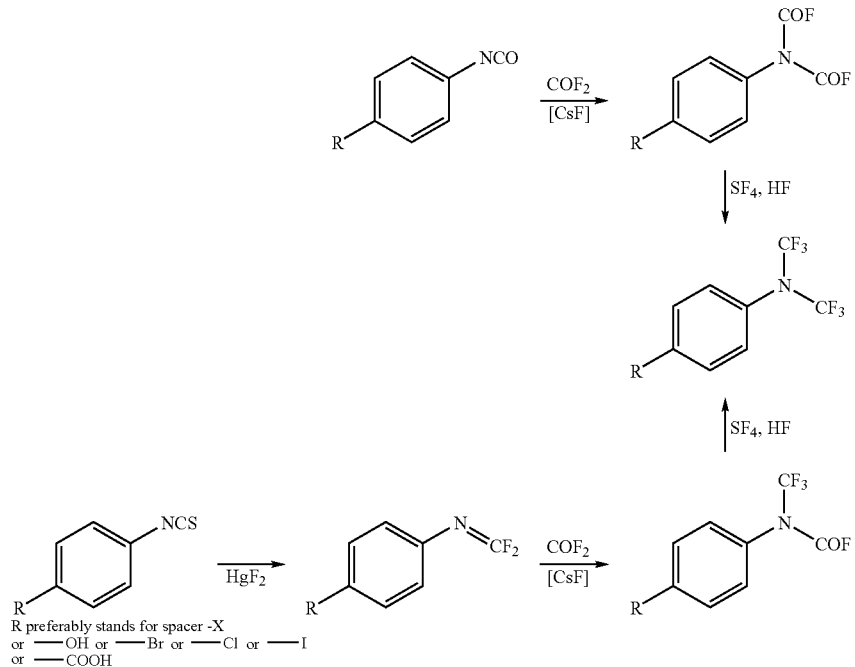

R preferably stands for spacer -X
or —OH or —Br or —Cl or —I
or —COOH

An alternative route for the preparation of the bistrifluoromethylanilines starts from aromatic aldehydes and is described in detail in R. E. Banks, J. Chem, Soc. Perkin Trans. 1 (1973) 80-82:

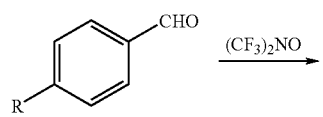

The following schemes show chain extensions, which can be carried out independently of Rf:

Chain Extension by Cross-Metathesis:

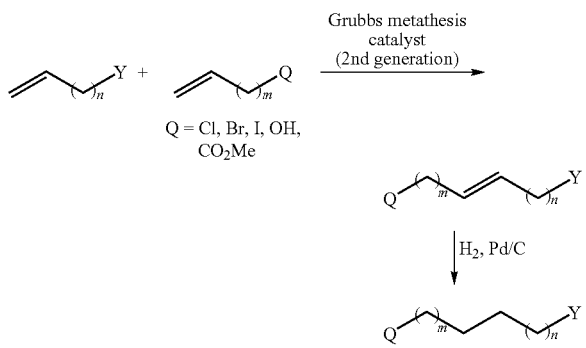

Chain Extension by Free-Radical Thiol Addition Reaction:

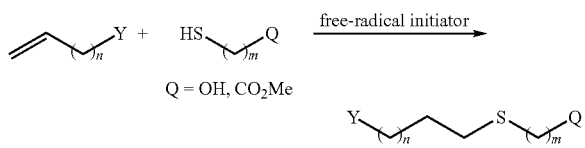

Chain Extension by Wittig Reaction:

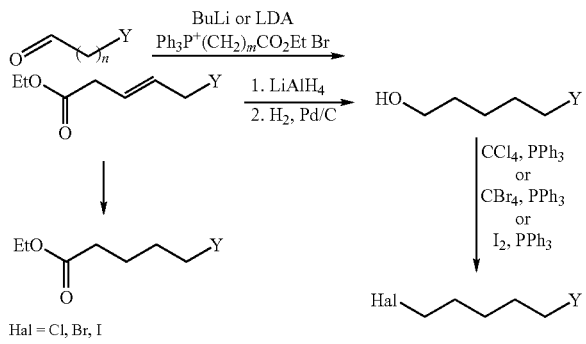

Chain Extension by Williamson Ether Synthesis:

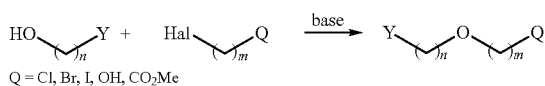

Chain Extension by Thioether Synthesis:

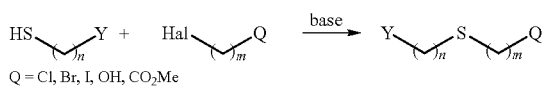

In addition, chain extensions are possible/can be carried out via ester or amide formation.

The corresponding disclosure of the said methods in the references cited here thus expressly also belongs to the disclosure content of the present application.

The choice of suitable solvents and reaction conditions presents the person skilled in the art in the case of the said reactions with absolutely no difficulties (Organikum: Organisch-Chemisches Grundpraktikum [Basic Practical Organic Chemistry], 16th Edn., VEB Deutscher Verlag der Wissenschaften, Berlin, 1986).

The invention furthermore relates to sulfonated fatty acid esters containing at least one group Y, where Y stands for $CF_3-(CH_2)_a-O-$, $SF_5-$, $CF_3-(CH_2)_a-S-$, $CF_3CF_2S-$, $[CF_3-(CH_2)_a]_2N-$ or $[CF_3-(CH_2)_a]NH-$, where a stands for an integer selected from the range from 0 to 5 or

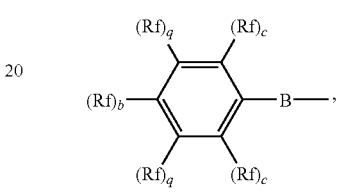

where
Rf stands for $CF_3-(CH_2)_r-$, $CF_3-(CH_2)_r-O-$, $CF_3-(CH_2)_r-S-$, $CF_3CF_2-S-$, $SF_5-(CH_2)_r-$ or $[CF_3-(CH_2)_r]_2N-$, $[CF_3-(CH_2)_r]NH-$ or $(CF_3)_2N-(CH_2)_r-$,
B stands for a single bond, O, NH, NR, $CH_2$, C(O)—O, C(O), S, $CH_2$—O, O—C(O), N—C(O), C(O)—N, O—C(O)—N, N—C(O)—N, O—$SO_2$ or $SO_2$—O,
R stands for alkyl having 1 to 4 C atoms,
b stands for 0 or 1 and c stands for 0 or 1,
q stands for 0 or 1, where at least one radical from b and q stands for 1, and
r stands for 0, 1, 2, 3, 4 or 5.

In the group Y, a preferably stands for 0, 1 or 2, particularly preferably for 0 or 2, very particularly preferably for 0, and r preferably stands for 0 to 3, in particular 0 to 1.

In a variant of the present invention, it is preferred for q in the group Y to stand for 0 and for at least one c and/or b each to stand for 1. It is particularly preferred for all c and b to stand for 1, i.e. the aromatic rings are substituted by fluorine groups in the o- and/or p-position, in particular in the o,p,o-position.

In a further variant of the invention, it is preferred for all q and b each to stand for 0 and for at least one c to stand for 1. It is particularly preferred for both c to stand for 1, i.e. the aromatic rings are substituted by fluorine groups in the o-position, in particular in the o,o-position.

In a further variant of the invention, it is preferred for all C and q each to stand for 0 and for b to stand for 1, i.e. the aromatic rings are substituted by fluorine groups in the p-position.

In a preferred embodiment, the sulfonated radical can be described by the sub-formula

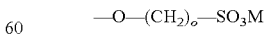

where
o=1, 2, 3, 4, 5 or 6, preferably 2 or 4, and
M=metal cation.

In the above-mentioned sub-formula, M denotes a metal cation, in particular selected from an alkali metal cation, an alkaline-earth metal cation or an ammonium ion. The lithium, sodium or potassium cation or $NH_4^+$ is preferably used for M.

In a preferred variant of the invention, the group Y, as defined above, consists of the sub-group $CF_3$—O—, $SF_5$—, $CF_3$—S—, $CF_3CF_2S$—, $(CF_3)_2N$— or

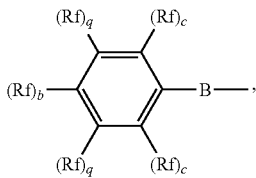

where
Rf stands for $CF_3$—$(CH_2)_r$—, $CF_3$—$(CH_2)_r$—O—, $CF_3$—$(CH_2)_r$—S—, $CF_3CF_2$—S—, $SF_5$—$(CH_2)_r$— or $[CF_3$—$(CH_2)_r]_2N$—, $[CF_3$—$(CH_2)_r]NH$— or $(CF_3)_2N$—$(CH_2)_r$—,
B stands for a single bond, O, NH, NR, $CH_2$, C(O)—O, C(O), S, $CH_2$—O, O—C(O), N—C(O), C(O)—N, O—C(O)—N, N—C(O)—N, O—$SO_2$ or $SO_2$—O,
R stands for alkyl having 1 to 4 C atoms,
b stands for 0 or 1 and c stands for 0 or 1,
q stands for 0 or 1, where at least one radical from b and q stands for 1, and
r stands for 0.

Rf preferably stands for $CF_3$—$(CH_2)_r$—, $CF_3$—$(CH_2)_r$—O—, $CF_3$—$(CH_2)_r$—S or $[CF_3$—$(CH_2)_r]_2N$—. A preferred variant of the invention encompasses fluorine groups, also abbreviated to Rf below, in which r stands for 0, 1, 2 or 3, in particular for 0, 1 or 2, where r preferably stands for 0.

In a particularly preferred embodiment of the present invention, Rf stands for $CF_3$—, $CF_3$—O—, $CF_3$—$CH_2$—$CH_2$—O—, $CF_3$—S—, $CF_3CF_2$—S—, $SF_5$—, $CF_3$—$CH_2$—$CH_2$—S—, $(CF_3)_2$—N— and $(CF_3$—$CH_2$—$CH_2)_2$—N—, in particular for $CF_3$—, $CF_3$—O—, $CF_3$—S— and $(CF_3)_2$—N—.

A further preferred variant of the invention encompasses the groups Rf which are equal to $CF_3$—, $CF_3$—S—, $CF_3CF_2$—S—, $SF_5$— or $(CF_3)_2N$—.

Particularly preferred groups B are O, S, $CH_2O$, $CH_2$, C(O) and OC(O). In particular, B equal to O and OC(O) are preferred.

A particularly preferred variant of the invention encompasses the groups Y which are equal to $CF_3$—Ar—O, $CF_3$—O—Ar—O, $CF_3$—$CH_2$—$CH_2$—O—Ar—O, $CF_3$—S—Ar—O, $CF_3CF_2$—S—Ar—O, $SF_5$—Ar—O, $CF_3$—$CH_2$—$CH_2$—S—Ar—O, $(CF_3)_2$—N—Ar—O, $(CF_3$—$CH_2$—$CH_2)_2$—N—Ar—O, $CF_3$—Ar—OC(O), $CF_3$—O—Ar—OC(O), $CF_3$—$CH_2$—$CH_2$—O—Ar—OC(O), $CF_3$—S—Ar—OC(O), $CF_3CF_2$—S—Ar—OC(O), $SF_5$—Ar—OC(O), $CF_3$—$CH_2$—$CH_2$—S—Ar—OC(O), $(CF_3)_2$—N—Ar—OC(O) and $(CF_3$—$CH_2$—$CH_2)_2$—N—Ar—OC(O), in particular equal to $CF_3$—Ar—O, $CF_3$—O—Ar—O, $CF_3$—S—Ar—O, $(CF_3)_2$—N—Ar—O, $CF_3$—Ar—OC(O), $CF_3$—O—Ar—OC(O), $CF_3$—S—Ar—OC(O) and $(CF_3)_2$—N—Ar—OC(O).

A particularly preferred variant of the invention encompasses Y equal to $CF_3$—Ar—O and $CF_3$—Ar—OC(O).

In a variant of the present invention, it is preferred for q to stand for 0 and for at least one c and/or b each to stand for 1. It is particularly preferred for all c and b to stand for 1, i.e. the aromatic rings are substituted by fluorine groups in the o,p,o-position.

In a further variant of the invention, it is preferred for all q and b each to stand for 0 and for at least one c to stand for 1.

It is particularly preferred for both c to stand for 1, i.e. the aromatic rings are substituted by fluorine groups in the o,o-position.

In a further variant of the invention, it is preferred for all c and q each to stand for 0 and for b to stand for 1, i.e. the aromatic rings are substituted by fluorine groups in the p-position.

Particular preference is given to the use of compounds which have a combination of the variables in their preferred or particularly preferred ranges.

Further preferred combinations are disclosed in the claims.

The particularly preferred compounds of the sulfonated fatty acid esters include the following compounds:

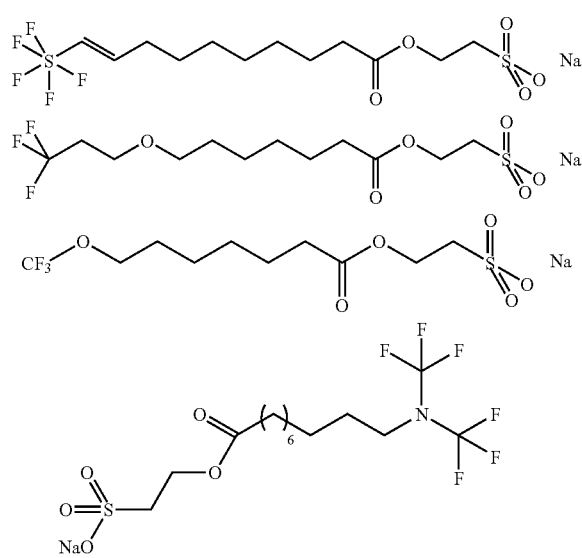

The sulfonated fatty acid esters containing at least one group Y, preferably arranged terminally to the ester function, can be obtained by reaction of a fatty acid containing at least one group Y, as described above for the fatty acid esters of the polyols (points 1 to 7 and the associated schemes), with a sodium salt of a hydroxysulfonic acid having 1 to 6 C atoms.

The hydroxysulfonic acids are commercially available or accessible by known synthesis.

The invention furthermore relates to sulfonated fatty acid amides containing at least one group Y, where Y stands for $CF_3$—$(CH_2)_a$—O—, $SF_5$—, $CF_3$—$(CH_2)_a$—S—, $CF_3CF_2S$—, $[CF_3$—$(CH_2)_a]_2N$— or $[CF_3$—$(CH_2)_a]NH$—, where a stands for an integer selected from the range from 0 to 5 or

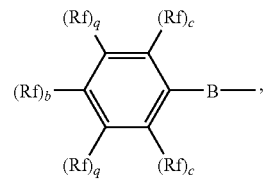

where
Rf=$CF_3$—$(CH_2)_r$—, $CF_3$—$(CH_2)_r$—O—, $CF_3$—$(CH_2)_r$—S—, $CF_3CF_2$—S—, $SF_5$—$(CH_2)_r$— or $[CF_3$—$(CH_2)_r]_2N$—, $[CF_3$—$(CH_2)_r]NH$— or $(CF_3)_2N$—$(CH_2)_r$—,
B stands for a single bond, O, NH, NR, $CH_2$, C(O)—O, C(O), S, $CH_2$—O, O—C(O), N—C(O), C(O)—N, O—C(O)—N, N—C(O)—N, O—$SO_2$ or $SO_2$—O, R stands for alkyl having 1 to 4 C atoms,
b stands for 0 or 1 and c stands for 0 or 1,
q stands for 0 or 1, where at least one radical from b and q stands for 1, and
r stands for 0, 1, 2, 3, 4 or 5.

In a preferred embodiment, the sulfonated radical can be described by the sub-formula

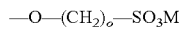

where
o=1, 2, 3, 4, 5 or 6, preferably 2 or 4 and
M=metal cation.

In the above-mentioned sub-formula, M denotes a metal cation, in particular selected from an alkali metal cation, an alkaline-earth metal cation or an ammonium ion. The lithium, sodium or potassium cation or $NH_4^+$ is preferably used for M.

In a preferred variant of the invention, the group Y, as defined above, consists of the sub-group $CF_3$—O—, $SF_5$—, $CF_3$—S—, $CF_3CF_2S$—, $(CF_3)_2N$— or

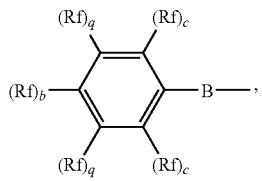

where
Rf stands for $CF_3$—$(CH_2)_r$—, $CF_3$—$(CH_2)_r$—O—, $CF_3$—$(CH_2)_r$—S—, $CF_3CF_2$—S—, $SF_5$—$(CH_2)_r$— or [$CF_3$—$(CH_2)_r$]$_2$N—, [$CF_3$—$(CH_2)_r$]NH— or $(CF_3)_2N$—$(CH_2)_r$—,
B stands for a single bond, O, NH, NR, $CH_2$, C(O)—O, C(O), S, $CH_2$—O, O—C(O), N—C(O), C(O)—N, O—C(O)—N, N—C(O)—N, O—$SO_2$ or $SO_2$—O,
R stands for alkyl having 1 to 4 C atoms,
b stands for 0 or 1 and c stands for 0 or 1,
q stands for 0 or 1, where at least one radical from b and q stands for 1, and
r stands for 0.

Rf preferably stands for $CF_3$—$(CH_2)_n$—, $CF_3$—$(CH_2)_r$—O—, $CF_3$—$(CH_2)_r$—S or [$CF_3$—$(CH_2)_r$]$_2$N—. A preferred variant of the invention encompasses fluorine groups, also abbreviated to Rf below, in which r stands for 0, 1, 2 or 3, in particular for 0, 1 or 2, where r preferably stands for 0.

In a particularly preferred embodiment of the present invention, Rf stands for $CF_3$—, $CF_3$—O—, $CF_3$—$CH_2$—$CH_2$—O—, $CF_3$—S—, $CF_3CF_2$—S—, $SF_5$—, $CF_3$—$CH_2$—$CH_2$—S—, $(CF_3)_2$—N— and $(CF_3$—$CH_2$—$CH_2)_2$—N—, in particular for $CF_3$—, $CF_3$—O—, $CF_3$—S— and $(CF_3)_2$—N—.

A further preferred variant of the invention encompasses the groups Rf which are equal to $CF_3$—, $CF_3$—S—, $CF_3CF_2$—S—, $SF_5$— or $(CF_3)_2N$—.

Particularly preferred groups B are O, S, $CH_2O$, $CH_2$, C(O) and OC(O). In particular, B equal to O and OC(O) are preferred.

A particularly preferred variant of the invention encompasses the groups Y which are equal to $CF_3$—Ar—O, $CF_3$—O—Ar—O, $CF_3$—$CH_2$—$CH_2$—O—Ar—O, $CF_3$—S—Ar—O, $CF_3CF_2$—S—Ar—O, $SF_5$—Ar—O, $CF_3$—$CH_2$—$CH_2$—S—Ar—O, $(CF_3)_2$—N—Ar—O, $(CF_3$—$CH_2$—$CH_2)_2$—N—Ar—O, $CF_3$—Ar—OC(O), $CF_3$—O—Ar—OC(O), $CF_3$—$CH_2$—$CH_2$—O—Ar—OC(O), $CF_3$—S—Ar—OC(O), $CF_3CF_2$—S—Ar—OC(O), $SF_5$—Ar—OC(O), $CF_3$—$CH_2$—$CH_2$—S—Ar—OC(O), $(CF_3)_2$—N—Ar—OC(O) and $(CF_3$—$CH_2$—$CH_2)_2$—N—Ar—OC(O), in particular equal to $CF_3$—Ar—O, $CF_3$—O—Ar—O, $CF_3$—S—Ar—O, $(CF_3)_2$—N—Ar—O, $CF_3$—Ar—OC(O), $CF_3$—O—Ar—OC(O), $CF_3$—S—Ar—OC(O) and $(CF_3)_2$—N—Ar—OC(O).

A particularly preferred variant of the invention encompasses Y equal to $CF_3$—Ar—O and $CF_3$—Ar—OC(O).

In a variant of the present invention, it is preferred for q to stand for 0 and for at least one c and/or b each to stand for 1. It is particularly preferred for all c and b to stand for 1, i.e. the aromatic rings are substituted by fluorine groups in the o,p,o-position.

In a further variant of the invention, it is preferred for all q and b each to stand for 0 and for at least one c to stand for 1. It is particularly preferred for both c to stand for 1, i.e. the aromatic rings are substituted by fluorine groups in the o,o-position.

In a further variant of the invention, it is preferred for all c and q each to stand for 0 and for b to stand for 1, i.e. the aromatic rings are substituted by fluorine groups in the p-position.

Particular preference is given to the use of compounds which have a combination of the variables in their preferred or particularly preferred ranges.

Further preferred combinations are disclosed in the claims.

The particularly preferred compounds of the sulfonated fatty acid amides include the following compounds:

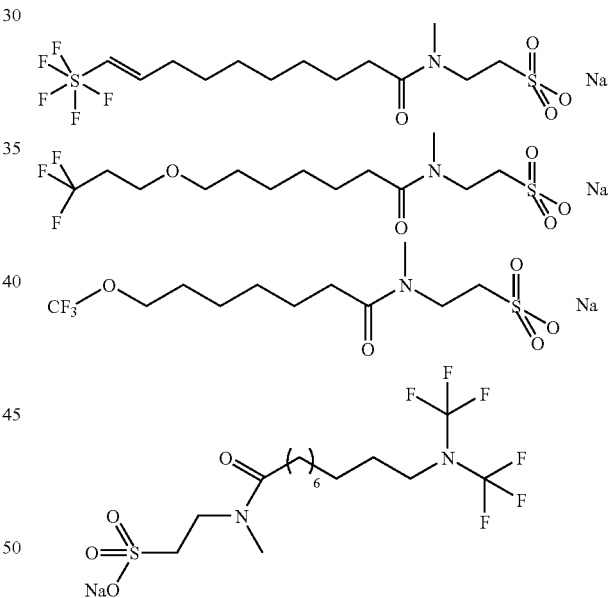

The sulfonated fatty acid amides containing at least one group Y, preferably arranged terminally to the amide function, can be obtained by reaction of a fatty acid containing at least one group Y, as described above for the fatty acid esters of the polyols (points 1 to 7 and the associated schemes), with a sodium salt of an aminosulfonic acid having 1 to 6 C atoms.

The aminosulfonic acids are commercially available or accessible by known synthesis.

Advantages of the compounds according to the invention or the compositions or agents according to the invention may be, in particular:
a surface activity which may be equal or superior to the conventional hydrocarbon surfactants with respect to efficiency and/or effectiveness and/or biological and/or abiotic degradability of the substances without the formation of persistent, perfluorinated degradation products and/or good processability in formulations and/or storage stability.

The compounds which can be used in accordance with the invention as surfactants are particularly suitable for use as hydrophobicising agents or oleophobicising agents.

Areas of use are, for example, the surface modification of textiles, paper, glass, porous building materials or adsorbents. In paints, coatings, inks, photographic coatings (for photographic plates, films and papers), special coatings for semiconductor photolithography (photoresists, top antireflective coatings, bottom antireflective coatings) or other preparations for surface coating, the compounds according to the invention and the compounds to be employed in accordance with the invention can advantageously be employed with one or more of the following functions: antifogging agent, dispersant, emulsion stabiliser, antifoam, deaerating agent, antistatic, flame retardant, gloss enhancer, lubricant, pigment- or filler-compatibility enhancer, scratch-resistance enhancer, substrate adhesion enhancer, surface adhesion reducer, skin preventer, hydrophobicising agent, oleophobicising agent, UV stabiliser, wetting agent, flow-control agent, viscosity reducer, migration inhibitor, drying accelerator. In printing inks, the compounds according to the invention and the compounds to be employed in accordance with the invention can likewise advantageously be employed and have one or more of the following functions: antifoam, deaerating agent, friction-control agent, wetting agent, flow-control agent, pigment-compatibility enhancer, print-resolution enhancer, drying accelerator.

The present invention therefore furthermore relates to the use of the compounds according to the invention or the compounds to be employed in accordance with the invention as additives in preparations for surface coating, such as printing inks, paints, coatings, photographic coatings, special coatings for semiconductor photolithography, such as photoresists, top antireflective coatings, bottom antireflective coatings, or in additive preparations for addition to corresponding preparations.

A further use according to the invention of compounds according to the invention or compounds to be employed in accordance with the invention is the use as interface promoter or emulsifier. These properties can advantageously be utilised, in particular, for the preparation of fluoropolymers by means of emulsion polymerisation.

Compounds according to the invention and compounds to be employed in accordance with the invention can be employed as foam stabiliser, in particular in preparations which are known as "fire-extinguishing foams". The invention therefore furthermore relates to the use of compounds according to the invention or compounds to be employed in accordance with the invention as foam stabiliser and/or for supporting film formation, in particular in aqueous film-forming fire-extinguishing foams, both synthetic and also protein-based, and also for alcohol-resistant formulations (AFFF and AFFF-AR, FP, FFFP and FFFP-AR fire-extinguishing foams).

Compounds according to the invention and compounds to be employed in accordance with the invention can also be used as antistatics. The antistatic action is of particular importance in the treatment of textiles, in particular clothing, carpets and carpeting, upholstery in furniture and automobiles, non-woven textile materials, leather goods, papers and cardboard articles, wood and wood-based materials, mineral substrates, such as stone, cement, concrete, plaster, ceramics (glazed and unglazed tiles, earthenware, porcelain) and glasses, and for plastics and metallic substrates. The present application relates to the corresponding use.

For metallic substrates, the present invention additionally also relates to the use of compounds according to the invention in anticorrosion agents.

The present invention furthermore also relates to the use thereof as mould-release agents in plastics processing.

In general, compounds according to the invention and compounds to be employed in accordance with the invention are suitable as protection agents against spots and soiling, stain releases, antifogging agents, lubricants, and as abrasion-resistance and mechanical wear-resistance enhancers.

Compounds according to the invention and compounds to be employed in accordance with the invention can advantageously be employed as additives in cleaning compositions and spot removers for textiles (in particular clothing, carpets and carpeting, upholstery in furniture and automobiles) and hard surfaces (in particular kitchen surfaces, sanitary installations, tiles, glass) and in polishes and waxes (in particular for furniture, flooring and automobiles) with one or more of the following functions: wetting agent, flow-control agent, hydrophobicising agent, oleophobicising agent, protection agent against spots and soiling, lubricant, antifoam, deaerating agent, drying accelerator. In the case of cleaning compositions and spot removers, the use as detergent or dirt emulsifier and dispersant is also additionally an advantageous embodiment of the present invention. The invention therefore furthermore relates to the use of compounds according to the invention or compounds to be employed in accordance with the invention in cleaning compositions and spot removers or as wetting agent, flow-control agent, hydrophobicising agent, oleophobicising agent, protection agent against spots and soiling, lubricant, antifoam, deaerating agent or drying accelerator.

The compounds according to the invention and compounds to be employed in accordance with the invention can also advantageously be used as additives in polymeric materials (plastics) with one or more of the following functions: lubricant, internal-friction reducer, UV stabiliser, hydrophobicising agent, oleophobicising agent, protection agent against spots and soiling, coupling agent for fillers, flame retardant, migration inhibitor (in particular against migration of plasticisers), antifogging agent.

On use as additives in liquid media for cleaning, etching, reactive modification and/or substance deposition on metal surfaces (in particular also electroplating and anodisation) or semiconductor surfaces (in particular for semiconductor photolithography), compounds according to the invention and compounds to be employed in accordance with the invention act as developer, stripper, edge bead remover, etching and cleaning composition, as wetting agent and/or deposited film quality enhancer. In the case of electroplating processes (in particular chrome plating), the present invention additionally also relates to the function as fume inhibitor with or without foam action.

In addition, the compounds which can be used in accordance with the invention as surfactants are suitable for washing and cleaning applications, in particular of textiles. Cleaning and polishing of hard surfaces is also a possible area of application for the compounds which can be used in accordance with the invention as surfactants. Furthermore, the compounds which can be used in accordance with the invention as surfactants can advantageously be employed in cosmetic products, such as, for example, foam baths and hair shampoos, or as emulsifiers in creams and lotions. The compounds according to the invention and the compounds to be employed in accordance with the invention can likewise advantageously be employed as additives in hair- and body-care products (for example hair rinses and hair conditioners), with one or more of the following functions: wetting agent, foaming agent, lubricant, antistatic, skin-grease resistance enhancer.

Compounds according to the invention and compounds to be employed in accordance with the invention act as additives in herbicides, pesticides and fungicides with one or more of the following functions: substrate wetting agent, adjuvant, foam inhibitor, dispersant, emulsion stabiliser.

Compounds according to the invention and compounds to be employed in accordance with the invention can likewise beneficially be employed as additives in adhesives, with one or more of the following functions: wetting agent, penetration agent, substrate adhesion enhancer, antifoam. Compounds according to the invention and compounds to be employed in accordance with the invention can also serve as additives in lubricants and hydraulic fluids, with one or more of the following functions: wetting agent, corrosion inhibitor. In the case of lubricants, the use as dispersant (in particular for fluoropolymer particles) is additionally also an essential aspect On use as additives in putty and filling compositions, compounds according to the invention and compounds to be employed in accordance with the invention can act with one or more of the following functions: hydrophobicising agent, oleophobicising agent, protection agent against soiling, weathering-resistance enhancer, UV stabiliser, silicone bleeding inhibitor.

A further area of application for the compounds which can be used in accordance with the invention as surfactants is flotation, i.e. the recovery and separation of ores and minerals from dead rock. To this end, they are employed as additives in preparations for ore processing, in particular flotation and leaching solutions, with one or more of the following functions: wetting agent, foaming agent, foam inhibitor. A related use is also as additives in agents for the stimulation of oil wells, with one or more of the following functions: wetting agent, foaming agent, emulsifier.

In addition, they can be employed as additives in de-icing agents or icing inhibitors.

In addition, preferred compounds which can be used in accordance with the invention as surfactants can also be employed as emulsifiers or dispersion assistants in foods. Further fields of application are in metal treatment, as leather auxiliaries, construction chemistry and in crop protection.

Surfactants according to the invention are furthermore also suitable as antimicrobial active compound, in particular as reagents for antimicrobial surface modification.

The present invention relates to all uses mentioned here of compounds to be employed in accordance with the invention. The respective use of surfactants for the said purposes is known to the person skilled in the art, and consequently the use of the compounds to be employed in accordance with the invention presents no problems.

For the application, the compounds according to the invention are usually introduced into appropriately formulated preparations. The present invention likewise relates to corresponding compositions comprising at least one compound according to the invention. Such compositions preferably comprise a vehicle which is suitable for the particular application and optionally further specific active compounds and/or optionally assistants.

Preferred compositions here are paint and coating preparations, fire-extinguishing compositions, lubricants, washing and cleaning compositions, deicers or hydrophobicising agents for textile finishing or glass treatment. In a preferred variant of the invention, the compositions are hydrophobicising agents for finishing textiles and carpets.

For the hydrophobic finishing of textiles, hydrophobicising agents based on polysiloxanes, fluorinated hydrocarbons or mixtures of aluminium or zirconium salts with paraffins are generally employed (cf. in this respect "Hand-buch der Textilhilfsmittel" [Handbook of Textile Assistants], A. Chwala, V. Anger, Verlag Chemie, New York 1977, Chapter 3.24 "Phobiermittel" [Proofing Agents], pages 735 ff). The hydrophobic finishing of textiles, in particular in the case of weather-protection clothing, serves to make these either water-resistant or waterproof. The hydrophobicising agent is applied to the fibres of the textiles, where it aligns itself in such a way that the hydrophobic parts of the molecules are perpendicular to the fibre surface. In this way, the tendency of water to spread over the entire surface is greatly reduced. The water adopts a spherical shape owing to cohesion forces and runs off the textile surface in the form of beads.

Further areas of application for compositions according to the invention are paint and coating preparations, fire-extinguishing compositions (powders and foams), lubricants, washing and cleaning compositions and de-icers.

The compositions can be prepared by methods known per se; for example by mixing the compounds according to the invention with a vehicle which is suitable for the particular application and optionally further specific active compounds and optionally assistants. The compounds to be used in accordance with the invention can be prepared by methods known per se to the person skilled in the art from the literature.

Apart from the preferred compounds mentioned in the description, the use thereof, compositions and processes, further preferred combinations of the subject-matters according to the invention are disclosed in the claims.

The disclosures in the cited references thus expressly also belong to the disclosure content of the present application.

The following examples explain the present invention in greater detail without restricting the scope of protection. In particular, the features, properties and advantages described in the Examples of the compounds on which the particular examples are based can also be applied to other substances and compounds which are not mentioned in detail, but fall within the scope of protection, so long as nothing to the contrary is stated elsewhere. In addition, the invention can be carried out throughout the claimed range and is not restricted to the examples mentioned here.

EXAMPLES

List of abbreviations used:
Bn: benzyl
DBH: 1,3-dibromo-5,5-dimethylhydantoin
DCM: dichloromethane
DMAP: 4-(dimethylamino)pyridine
Me: methyl
MTB: methyl tert-butyl ether
RT room temperature (20° C.)
THF: tetrahydrofuran
PE: petroleum ether
DCC N,N'-dicyclohexylcarbodiimide
RT room temperature
TPAP tetra-n-propylammonium perruthenate
VE demineralised
TLC thin-layer chromatography
DIAD diisopropyl azodicarboxylate

Example 1

1. Synthesis of (E)-10-pentafluorosulfanyldec-9-enecarboxylic acid

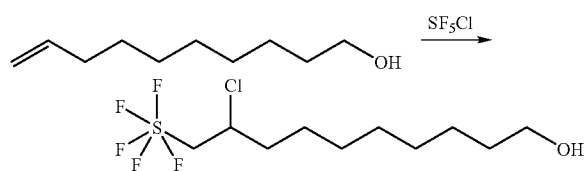

15 g of decenol are dissolved in 250 ml of DCM (dichloromethane) and cooled to −40° C. 27 g of SF$_5$Cl—previously condensed by cold trap—are passed into the apparatus as a gas. For activation, 2 ml of 1 M Et$_3$B solution are added. During passing-in of the gas, the batch becomes cloudy. The activation is repeated until the batch no longer warms when the gas is passed in. The mixture is stirred at the same temperature for a further two hours. The reaction mixture is hydrolysed by addition to ice/NaHCO$_3$ solution (saturated) and then adjusted to pH 10 using NaOH. The aqueous phase separated off is washed twice with MTB ether (MTB ether=methyl tert-butyl ether). The collected organic phases are extracted once with NaCl solution, dried over sodium sulfate, filtered and evaporated in a rotary evaporator. Chromatography gives the product in pure form.

Elimination:

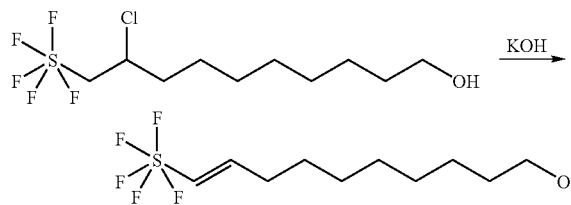

9 g of the starting material (28.2 mmol) are dissolved in 120 ml of ethanol in a 250 ml single-necked flask with reflux condenser, and KOH powder (4.75 g, 85 mmol, 3 eq) is subsequently added. The reaction mixture is stirred overnight, and subsequently evaporated, and water and MTB ether are added. After the phases have been separated, the aqueous phase is extracted 3 times with MTB ether, and the collected organic phases are washed with sat. NaCl solution, dried over Na$_2$SO$_4$, filtered and freed from solvent by distillation, giving 8.3 g of yellowish liquid. The Rf value is slightly higher (less polar substance) than the starting material.

Oxidation:

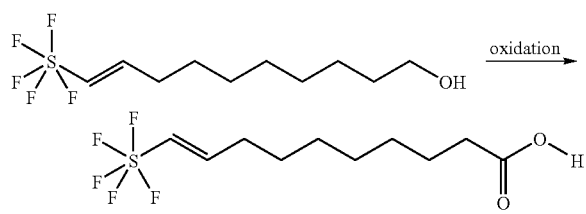

Literature: Tetrahedron Vol. 44, No. 9, pp. 2636, 1988

11.3 mmol of the alcohol are dissolved in a solvent mixture comprising carbon tetrachloride (40 ml), acetonitrile (40 ml) and water (50 ml), sodium metaperiodate (5.44 g, 25.4 mmol, 2.25 eq) and ruthenium(III) chloride (234 mg, 1.13 mmol, 0.1 eq) are then added, and the reaction mixture is stirred at 22° C.-26° C. (RT) for 3 hours. 50 ml of dichloromethane are then added to the reaction mixture, the phases are separated, and the aqueous phase is extracted a further twice with 50 ml of dichloromethane each time. The combined dichloromethane solutions are dried using sodium sulfate and filtered, and the solvent is removed by distillation. The product is obtained as an oily residue.

2. Esterification Using Sorbitol

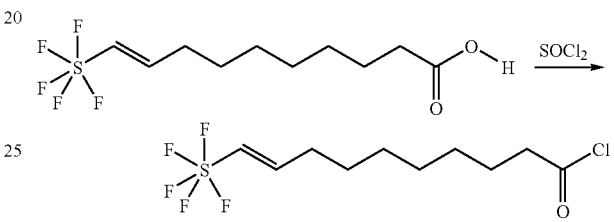

30 g of (E)-10-pentafluorosulfanyldec-9-enecarboxylic acid are initially introduced in 100 g of toluene, and 24 g of SOCl$_2$ are added. The reaction mixture is warmed to 70° C., and the excess of SOCl$_2$ and solvent is removed by distillation. The resultant acid chloride is employed in the subsequent acylation without further purification.

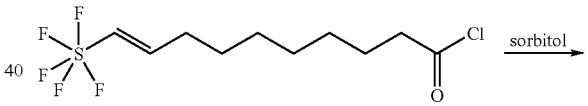

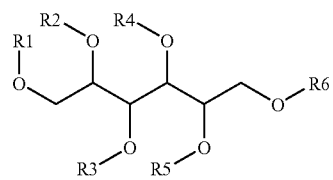

R1...R6 = H or

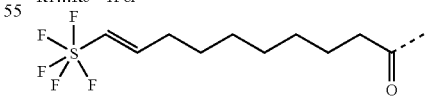

18 g of sorbitol are suspended in 150 g of THF (tetrahydrofuran), and 32 g of the acid chloride (1 equivalent) and 10 g of triethylamine are subsequently added. When the reaction is complete, the product mixture is isolated and purified by conventional laboratory methods.

The degree of acylation can be increased by using more acid chloride (2-20 equivalents).

A monoacylation preferably takes place for R1 or R6; a diacylation preferably takes place for R1 and R6.

Example 2

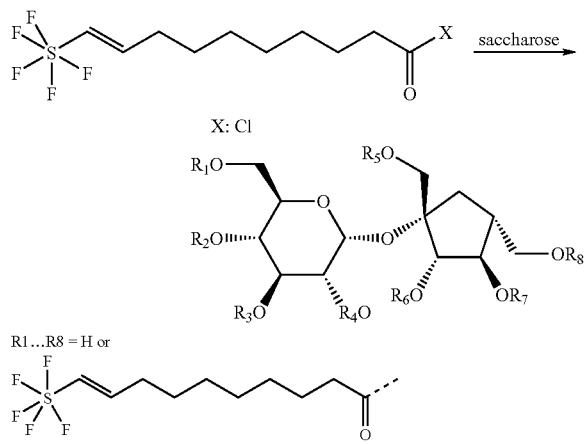

34 g of saccharose are suspended in 100 g of THF, and 31 g of (E)-10-pentafluorosulfanyldec-9-enecarbonyl chloride, prepared as in Example 1, and 10 g of triethylamine are subsequently added. When the reaction is complete, the product mixture is isolated and purified by conventional laboratory methods. The degree of acylation can be increased by using more acid chloride (2-20 equivalents).

A monoacylation preferably takes place for R1 or R5 or R8; a diacylation preferably takes place for R1/R5 or R1/R8 or R5/R6.

Example 3

1. Synthesis of methyl 7-(3,3,3-trifluoropropoxy)heptanoate

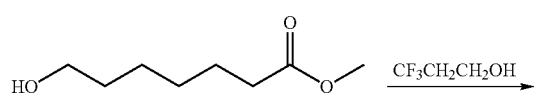

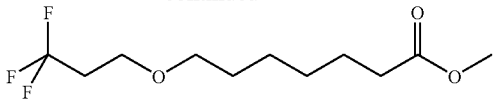

3,3,3-Trifluoropropanol (10 ml, 110 mmol), methyl 7-hydroxyheptanoate (133 mmol, 1.2 eq), triphenylphosphine (35 g, 133 mmol, 1.2 eq) are initially introduced in 37 ml of THF in a round-bottomed flask and introduced into an ultrasound bath for a few minutes in order to mix the substances. During the exposure to ultrasound, DIAD (26.5 ml, 133 mmol, 1.2 eq) is very slowly added dropwise (temperature rises), and the reaction mixture is left under ultrasound for 15 min. A TLC sample is taken and subsequently left in the ultrasound bath for a further 2 hours.

The solvent is removed in a rotary evaporator. 90 ml of cold MTB ether are subsequently added, during which triphenylphosphine oxide precipitates out. The solid is filtered off with suction, and the solution is stored in a refrigerator over the weekend in order that the remainder also precipitates. The remaining solid is filtered off with suction, and the residue is washed with MTB. The product solution is evaporated in a rotary evaporator and purified by column chromatography.

2. Synthesis of 7-(3,3,3-trifluoropropoxy)heptanoic acid

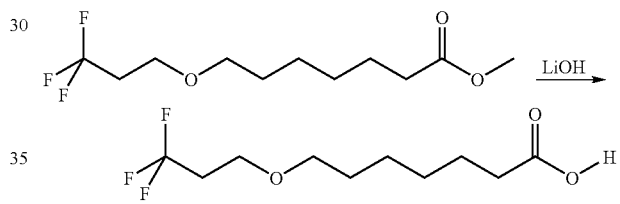

Methyl 7-(3,3,3-trifluoropropoxy)heptanoate (50 mmol) is dissolved in 500 ml of THF in a round-bottomed flask, and solid lithium hydroxide (65 mmol, 1.3 eq) is added in portions at RT. The mixture is stirred at RT for 1 hr, and 100 ml of water and 200 ml of MTB ether are subsequently added. The mixture is acidified to pH 1 using aqueous HCl, the phases are separated, and the aqueous phase is extracted a number of times with MTB. The combined organic phases are dried over sodium sulfate and evaporated in a rotary evaporator. The carboxylic acid formed in this way is employed directly in the subsequent step.

3. Esterification Using Sorbitol

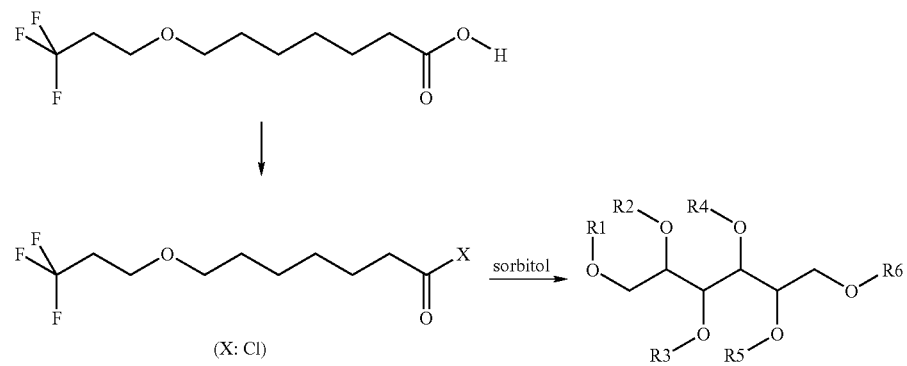

-continued

R1...R6 = H or
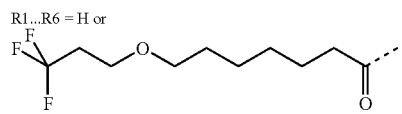

Analogously to Example 1, firstly 24 g of 7-(3,3,3-trifluoropropoxy)heptanoic acid are initially introduced in 100 g of toluene and reacted with 24 g of SOCl$_2$, and the acid chloride forming is esterified using 18 g of sorbitol in THF and in the presence of triethylamine.

Example 4

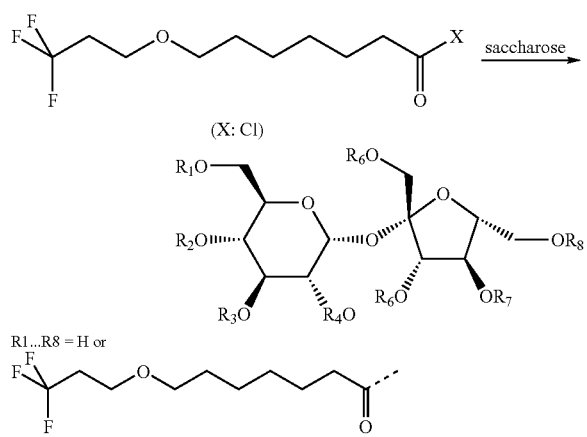

(X: Cl)

R1...R8 = H or

Analogously to Example 2, 34 g of saccharose in 100 g of THF are reacted with 30 g of 7-(3,3,3-trifluoropropoxy)heptanoyl chloride, prepared as in Example 3, and 10 g of triethylamine. When the reaction is complete, the product mixture is isolated and purified using conventional laboratory methods. The degree of acylation can be increased by using more acid chloride (2-20 equivalents).

Example 5

1. Synthesis of the Acid

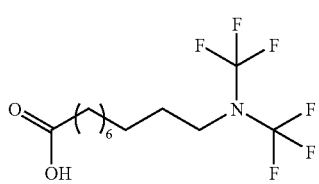

a: Preparation of the Ammonium Salt:

0.052 g (0.18 mmol) of CF$_3$SO$_2$N(CF$_3$)$_2$ is added at −40° C. to a solution of 0.017 g (0.18 mmol) of (CH$_3$)$_4$N$^+$F$^-$ in 0.5 ml of dry dichloromethane. The reaction solution is warmed to room temperature and diluted with the same amount of dry acetonitrile. Removal of the solvent by distillation in a dry argon atmosphere gives 0.037 g of a colourless, highly hygroscopic material in a yield of 90.2%.

19F NMR (CCl$_3$F): −40.8 s; melting point: 120-125° C.

b: Preparation of the Allyl Compounds:

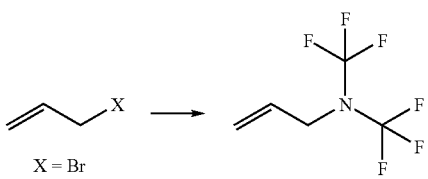

X = Br

A mixture of 0.837 g (2.12 mmol) of (CH$_3$)$_4$$^+$N(CF$_3$)$_2$$^-$ and 0.196 g (1.62 mmol) of allyl bromide is heated under reflux under an argon atmosphere for a few hours. When the reaction is complete, the product is removed by distillation.

c: Chain Extension

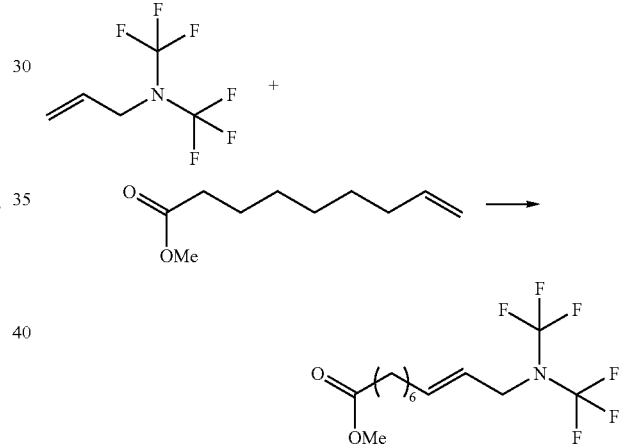

The allylamine derivative (4.2 g; 21.8 mmol) and subsequently the Grubbs II metathesis catalyst (0.9 g; 1 mmol) are added to a solution of the olefinic methyl ester (28.1 mmol) in 70 ml of dichloromethane.

The mixture is heated under reflux for 17 hrs.

The mixture is subsequently evaporated in a rotary evaporator and purified over a column. In order to remove the catalyst completely, the product is chromatographed again, giving the coupled product.

d. Hydrogenation of the Double Bond

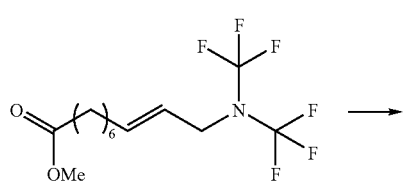

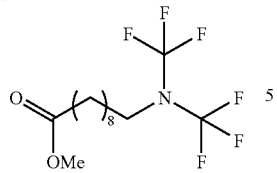

The methyl ester (27 mmol) is taken up in 250 ml of THF, and 5% palladium on active carbon (10 mol %) is added. After the hydrogen atmosphere has been applied (increased pressure), the reaction mixture is stirred for 3 hrs. and worked up when the reaction is complete. To this end, the catalyst is filtered off under a protective-gas atmosphere, and the solution is evaporated in a rotary evaporator.

The product can be employed directly in the subsequent step.

e: Preparation of the Acid

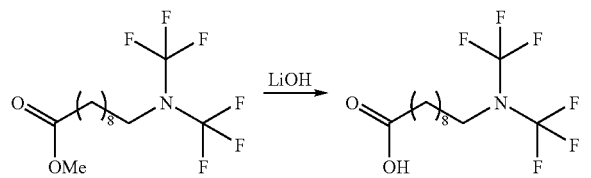

10 mmol of the methyl ester are dissolved in 100 ml of THF, and solid lithium hydroxide (13 mmol, 1.3 eq) is added in portions at RT. The mixture is stirred at RT for 1 hr., and 40 ml of water and 100 ml of MTB ether are subsequently added. The mixture is acidified to pH 1 using aqueous HCl, the phases are separated, and the aqueous phase is extracted a number of times with MTB. The combined organic phases are dried over sodium sulfate and evaporated in a rotary evaporator. The carboxylic acid formed in this way is employed directly in the subsequent step.

2. Esterification

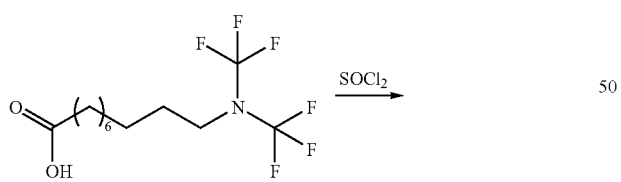

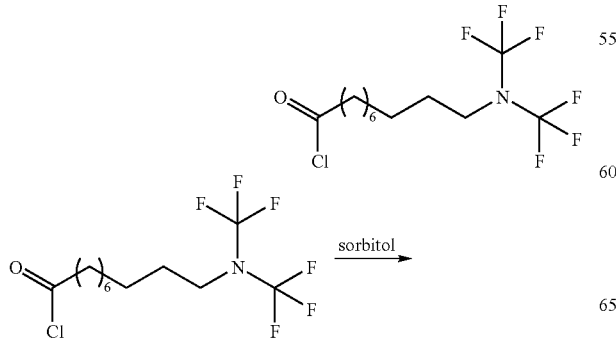

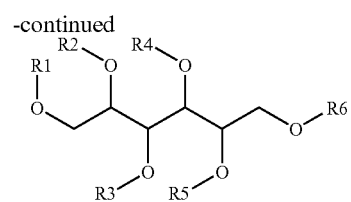

R1...R6 = H or

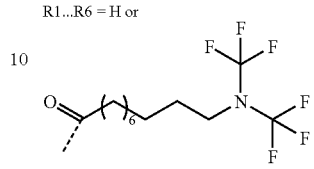

Analogously to Example 1, firstly 0.1 mol of the carboxylic acid are initially introduced in 100 g of toluene and reacted with 24 g of $SOCl_2$, and the acid chloride forming is esterified using 18 g of sorbitol in THF and in the presence of triethylamine.

Example 6

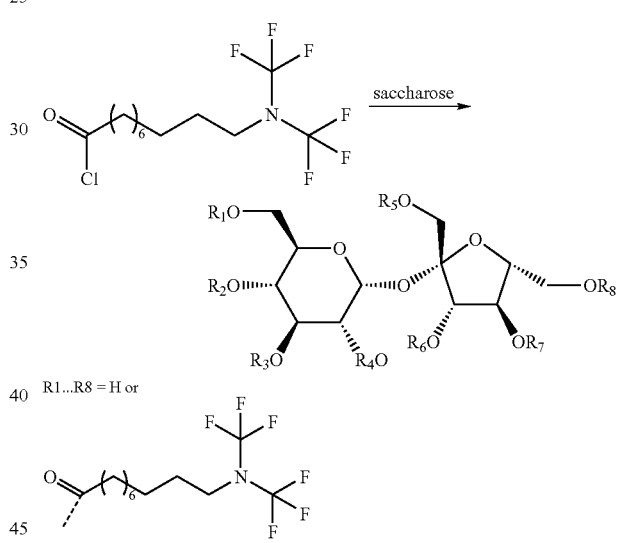

R1...R8 = H or

Analogously to Example 2, 34 g of saccharose in 100 g of THF are reacted with 0.1 mol of acid chloride, prepared as in Example 5, and 10 g of triethylamine. When the reaction is complete, the product mixture is isolated and purified using conventional laboratory methods. The degree of acylation can be increased by using more acid chloride (2-20 equivalents).

Example 7

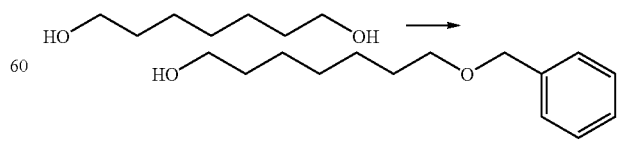

Sodium hydride (92 g, 2.3 mol, 1.36 eq) is suspended in 1200 ml of THF and cooled to 0° C. Heptane-1,7-diol (224 g, 1.7 mol) dissolved in 400 ml of THF is added dropwise to this suspension (note: $H_2$ evolution). The reaction mixture is warmed to room temperature and stirred for a further 3 hrs. Benzyl bromide (251.3 ml, 2.11 mol, 1.25 eq) and tetrabutylammonium iodide (32 g, 85 mmol, 0.05 eq) are subsequently added, and the mixture is stirred overnight (9 hrs.).

For work-up, the reaction mixture is quenched using 1200 ml of ice-water, the organic phase is separated off, the aqueous phase is extracted twice with MTB ether, and the combined organic extracts are washed with saturated NaCl solution. The organic phase is dried and evaporated in a rotary evaporator, giving the crude product, which is purified over silica gel.

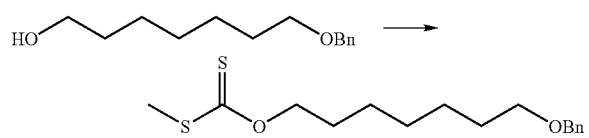

200 ml of THF and 10.15 g of NaH (253 mmol, 1.2 eq) are initially introduced into a 1 l four-necked glass apparatus which has been flushed with nitrogen, and cooled to −25° C. with stirring.

7-Benzyloxyheptan-1-ol (211 mmol, 1 eq) is mixed with 100 ml of THF and added dropwise over the course of 30 min (rinsed with 50 ml of THF), during which the internal temperature is kept at 0-5° C. The reaction mixture is then warmed to RT over the course of 30 min.

The mixture is stirred at RT for a further 120 min and subsequently cooled to −25° C. Carbon disulfide (32.1 g; 421.6 mmol; 2 eq) is added dropwise over the course of 10 min, during which the reaction mixture warms to 0° C. The mixture is stirred at 0° C. for a further 2.5 h. The colour of the reaction mixture changes from pale-brown to brown.

For the addition of methyl iodide, the mixture is re-cooled to −20° C., and MeI (35.9 g; 253 mmol; 1.2 eq) is subsequently added dropwise over the course of 5 min (strong evolution of heat: counter-cooled at −78° C.). The reaction mixture is slowly warmed to RT and stirred at this temperature for a further 24 hrs.

For work-up, the batch is then quenched using about 10% $NH_4Cl$ solution (200 ml).

The phases are separated. The water phase is washed twice with 100 ml of MTB ether. The organic phases are combined and subsequently washed once with 100 ml of about 10% saturated NaCl solution, and the phases are separated and dried using $Na_2SO_4$, filtered and evaporated to dryness in a rotary evaporator.

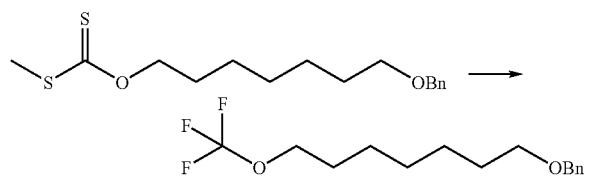

(HF)$_9$/Py (200 ml, 7.14 mol, 30 eq) and subsequently methyl xanthogenate (238 mmol) in 400 ml of DCM are added successively at −78° C. to a suspension of DBH (211 g, 738 mmol, 3.1 eq) in 1000 ml of DCM. The reaction mixture is stirred at −78° C. for a further 1 hr. and slowly warmed overnight with stirring (temperature in the morning 2° C.).

The reaction mixture is warmed to 19° C. and subsequently stirred at this temperature for about 1 hour.

It is subsequently re-cooled for hydrolysis.

640 ml of $NaHSO_3$ solution and 600 ml of 47% KOH are initially introduced in a 4 l four-necked flask and cooled to 0° C. The reaction mixture is subsequently sucked into the four-necked flask with the aid of a vacuum.

The entire mixture is made in portions. The maximum temperature should be 20° C.

The dark-red reaction solution becomes a yellowish suspension. Sufficient 47% KOH in 400 ml of demineralised water is added to this suspension until a pH of 7 has been reached. The suspension becomes thinner and thinner.

The phases are separated, and the aqueous phase is extracted twice with MTB ether. The collected organic phases are washed once with a sodium chloride solution, dried over sodium sulfate and subsequently evaporated. The crude product is stirred with active carbon and purified by column chromatography in petroleum ether.

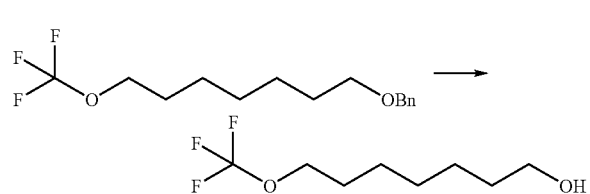

The benzyl ether (150 mmol) is taken up in ethanol (1000 ml), and 5% palladium (0.1 eq) on active carbon is added. After application of a hydrogen atmosphere (increased pressure), the progress of the reaction is investigated by TLC every hour. In order to complete the reaction, spent catalyst is filtered off and fresh catalyst is again added. When the reaction is complete, the palladium catalyst is filtered off, and the reaction mixture is evaporated. The crude product is employed directly in the next step.

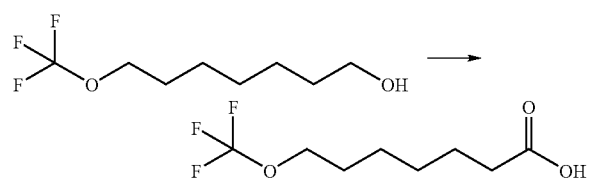

Analogously to Example 1, 22.6 mmol of the alcohol are dissolved in a solvent mixture comprising carbon tetrachloride (80 ml), acetonitrile (80 ml) and water (100 ml), sodium metaperiodate (10.88 g, 50.8 mmol, 2.25 eq) and ruthenium (III) chloride (468 mg, 2.26 mmol, 0.1 eq) are then added, and the reaction mixture is stirred at 22° C.-26° C. (RT) for 3 hours. 100 ml of dichloromethane are then added to the reaction mixture, the phases are separated, and the aqueous phase is post-extracted a further twice with 100 ml of dichloromethane each time. The combined dichloromethane solutions are dried using sodium sulfate and filtered, and the solvent is removed by distillation.

The carboxylic acid is obtained as an oily residue.

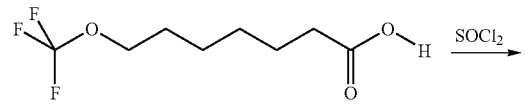

-continued

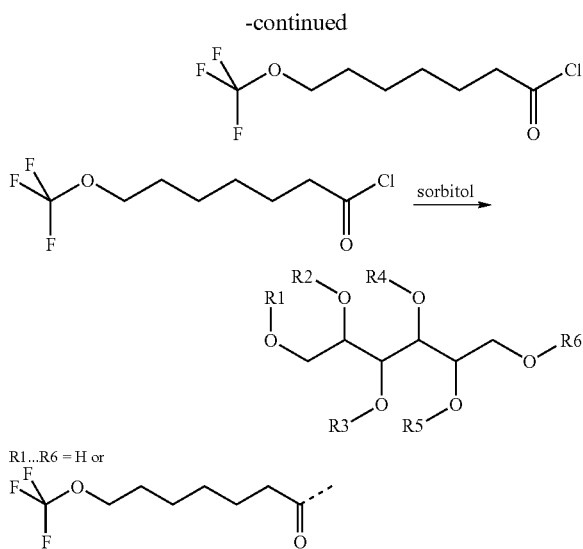

Analogously to Example 1, firstly 21 g of 7-trifluoromethoxyheptanoic acid are initially introduced in 100 g of toluene and reacted with 24 g of $SOCl_2$, and the acid chloride forming is esterified using 18 g of sorbitol in THF and in the presence of triethylamine.

Example 8

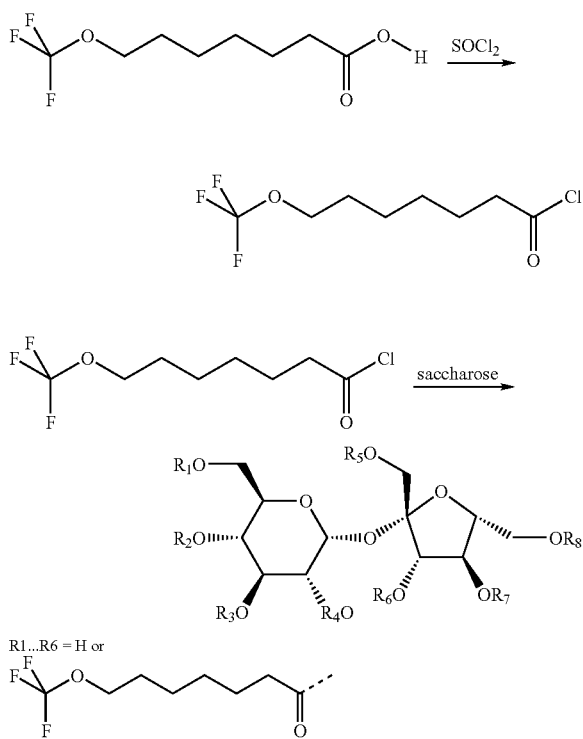

Analogously to Example 2, 34 g of saccharose in 100 g of THF are reacted with 0.1 mol of the acid chloride, prepared as in Example 7, and 10 g of triethylamine. When the reaction is complete, the product mixture is isolated and purified using conventional laboratory methods. The degree of acylation can be increased by using more acid chloride (2-20 equivalents).

Example A

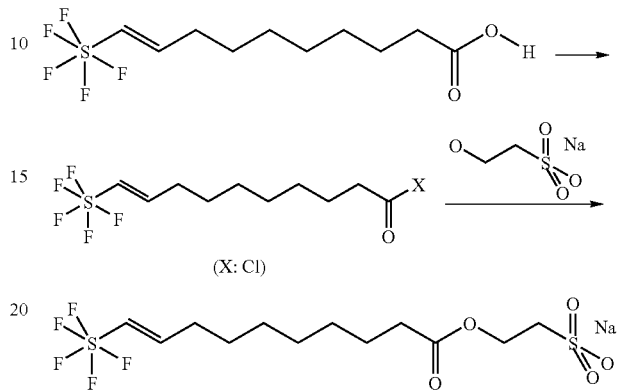

31 g of (E)-10-pentafluorosulfanyldec-9-enecarbonyl chloride, prepared as in Example 1, are dissolved in 100 g of THF, 2-hydroxyethanesulfonic acid Na salt (15 g) and triethylamine (10 g) are added, and the mixture is stirred at 30° C. for 6 hrs.

In order to isolate the product, the mixture is added to ice/methyl tert-butyl ether, the water phase is extracted with this solvent, and all org. phases are evaporated. Ethanol and then 1.2 equivalents of sodium hydroxide are added. The mixture is warmed briefly, and, after cooling, the crystals formed are isolated and dried.

Example B

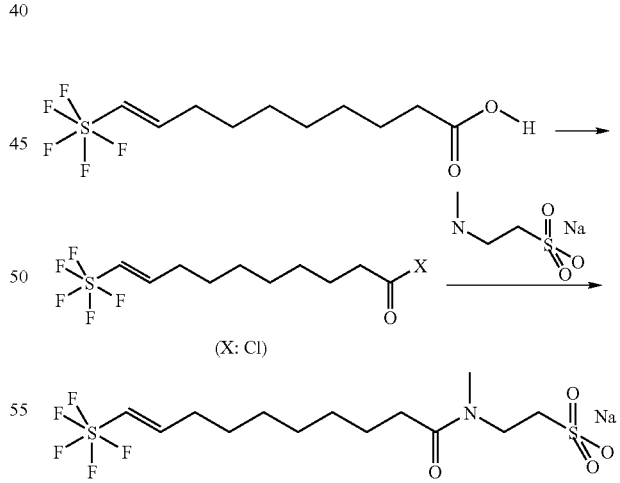

(E)-10-pentafluorosulfanyldec-9-enecarbonyl chloride, prepared as in Example 1, is dissolved in THF (100 g), 2-methylaminoethanesulfonic acid Na salt (16 g) and triethylamine (10 g) are added, and the mixture is stirred. In order to isolate the product, the mixture is added to ice/methyl tert-butyl ether, the water phase is extracted with the solvent, and all org. phases are evaporated. Ethanol and then 1.2 equiv. of sodium hydroxide are added. The mixture is warmed briefly, and, after cooling, the crystals formed are isolated and dried.

Example C

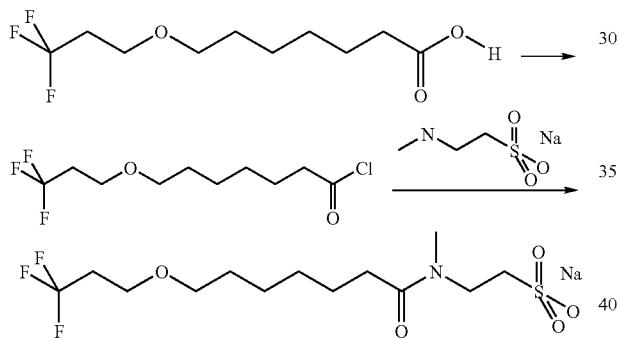

Analogously to Example A, 26 g of 7-(3,3,3-trifluoropropoxy)heptanoyl chloride in THF are reacted with 2-hydroxyethanesulfonic acid Na salt (15 g) and triethylamine (10 g). The crystals formed are isolated and dried.

Analogously to Example B, 26 g of 7-(3,3,3-trifluoropropoxy)heptanoyl chloride in THF are reacted with 2-methylaminoethanesulfonic acid Na salt (16 g) and triethylamine (10 g). The crystals formed are isolated and dried.

Example D

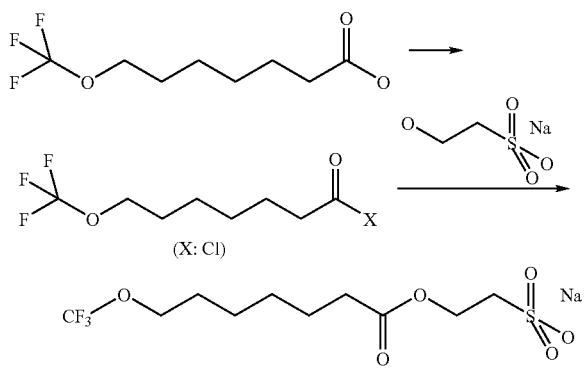

Analogously to Example A, 23 g of 7-(trifluoromethoxy)heptanoyl chloride, prepared as in Example 7, in THF are reacted with 2-hydroxyethanesulfonic acid Na salt (15 g) and triethylamine (10 g). The crystals formed are isolated and dried.

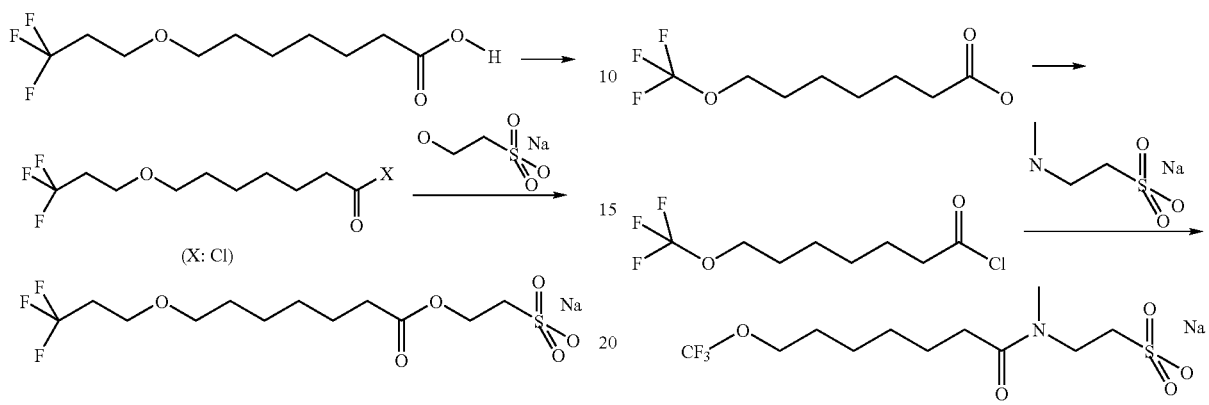

Analogously to Example B, 23 g of 7-(trifluoromethoxy)heptanoyl chloride in THF are reacted with 2-methylaminoethanesulfonic acid Na salt (16 g) and triethylamine (10 g). The crystals formed are isolated and dried.

Example E

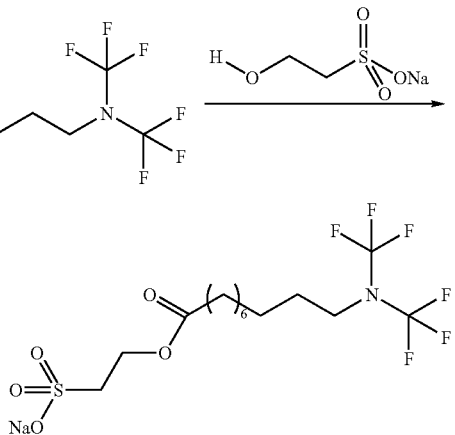

Analogously to Example A, 34 g of acid chloride, prepared as in Example 5, in THF are reacted with 2-hydroxyethanesulfonic acid Na salt (15 g) and triethylamine (10 g). The crystals formed are isolated and dried.

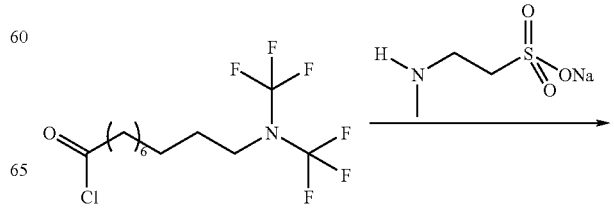

-continued

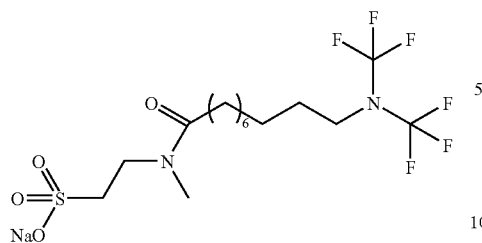

Analogously to Example B, 34 g of acid chloride, prepared as in Example 5, in THF are reacted with 2-methylaminoethanesulfonic acid Na salt (16 g) and triethylamine (10 g). The crystals formed are isolated and dried.

Example 9

Determination of the Biochemical Degradability

The biochemical degradability of the compounds is determined by the Zahn-Wellens test corresponding to the European Commission publication: Classification, Packaging and Labelling of Dangerous Substances in the European Union, Part II—Testing Methods, Annex V—Methods for the Determination of Physico-Chemical Properties, Toxicity and Ecotoxicity, Part B, Biochemical Degradability—Zahn-Wellens Test (C.9.), January 1997, pages 353-357.

| Batch volume: | 1.5 l |
| --- | --- |
| Activated sludge concentration: | 1 g of solids/l |
| Origin of the sludge: | treatment plant of Merck KGaA; Darmstadt (not adapted) |
| Amount of test substances used: | about 100 to 200 mg/l as DOC |
| Aeration: | with purified air |
| Work-up of the samples: | filtration (medium-hard filter) |
| Determination of the DOC: | by the difference method using a Dimatec instrument |

Further details on the method are given in the above publication and also the OECD Guideline for the testing of chemicals, section 3, degradation and accumulation, method 302 B, page 1-8, adopted: Jul. 17, 1992, the contents of which in this respect expressly belong to the disclosure content of the present application.

In addition, besides the degradation of the compound per se in the test, the degradation of the fluorine-containing groups is also observed via a fluoride determination:

| Method: | ion chromatography |
| --- | --- |
| Instrument: | Dionex 120 |
| Detector type: | conductivity detector |
| Column: | AS9HC |
| Eluent: | sodium carbonate solution, 9 mmol/l |
| Flow rate: | 1 ml/min |
| Literature: | EN ISO 10304-2 |

Example 10

Determination of the Surface Tension

| Instrument: | Krüss tensiometer (model K12) |
| --- | --- |
| Temperature of the measurement solutions: | 20° C. |
| Measurement module employed: | ring |
| Concentration of the measurement solutions: | about 0.5 to 3.0 g/l in deionised water |

Further details on the method are given by the European Commission publication: Classification, Packaging and Labelling of Dangerous Substances in the European Union, Part II—Testing Methods, Annex V—Methods for the Determination of Physico-Chemical Properties, Toxicity and Ecotoxicity, Part A, Surface Tension (A.5), January 1997, pages 51-57, and also the OECD Guideline for the testing of chemicals, section 1, physical-chemical properties, method 115, page 1-7, adopted: Jul. 27, 1995, the contents of which in this respect expressly belong to the disclosure content of the present application.

The invention claimed is:

1. A fatty acid ester of a polyol containing at least one group Y, which group Y is in the terminal position to the ester function, where
Y stands for $CF_3$—$(CH_2)_a$—O—, $SF_5$—, $CF_3$—$(CH_2)_a$—S—, $CF_3CF_2S$—, $[CF_3$—$(CH_2)_a]_2N$—$[CF_3$—$(CH_2)_a]$NH—, or

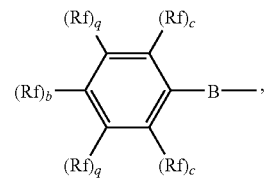

where
a stands for an integer selected from 0 to 5,
Rf stands for $CF_3$—$(CH_2)_r$—, $CF_3$—$(CH_2)_r$—O—, $CF_3$—$(CH_2)_r$—S—, $CF_3CF_2$—S—, $SF_5$—$(CH_2)_r$—, $[CF_3$—$(CH_2)_r]_2N$—, $[CF_3$—$(CH_2)_r]NH$— or $(CF_3)_2N$—$(CH_2)_r$—,
B stands for a single bond, O, NH, NR, $CH_2$, C(O)—O, C(O), S, $CH_2$—O, O—C(O), N—C(O), C(O)—N, O—C(O)—N, N—C(O)—N, O—$SO_2$ or $SO_2$—O,
R stands for alkyl having 1 to 4 C atoms,
b stands for 0 or 1,
c stands for 0 or 1,
q stands for 0 or 1, and
r stands for 0, 1, 2, 3, 4 or 5, and
where at least one of b and q stands for 1.

2. A compound according to claim 1, wherein the fatty acid radical may be saturated or unsaturated with 4 to 25 C atoms.

3. A compound according to claim 1, wherein the polyol radical is an —O—$CH_2$—$(CHOH)_n$—$CH_2$—OH radical, where n=1, 2, 3, 4 or 5, a monosaccharide radical, a disaccharide radical or an oligosaccharide radical.

4. A compound according to claim 1, wherein the fatty acid radical containing the group Y occurs at least once.

5. A compound according to claim 1, wherein the group Y denotes $CF_3$—$(CH_2)_a$—O—, where a=0, 1, 2, 3, 4 or 5.

6. A compound according to claim 1, wherein the group Y denotes $SF_5$.

7. A compound according to claim 1, wherein the group Y denotes $CF_3-(CH_2)_a-S-$, where a=0, 1, 2, 3, 4 or 5.

8. A compound according to claim 1, wherein the group Y denotes $CF_3-CF_2-S-$.

9. A compound according to claim 1, wherein the group Y denotes $[CF_3-(CH_2)_a]_2N-$, where a=0, 1, 2, 3, 4 or 5.

10. A compound according to claim 1, wherein the group Y denotes $[CF_3-(CH_2)_a]NH-$, where a=0, 1, 2, 3, 4 or 5.

11. A compound according to claim 1,
wherein the group Y denotes

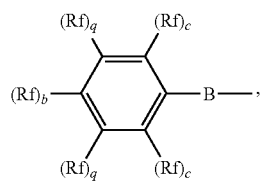

where
Rf stands for $CF_3-(CH_2)_r-$, $CF_3-(CH_2)_r-O-$, $CF_3-(CH_2)_r-S-$, $CF_3CF_2-S-$, $SF_5-(CH_2)_r-$, $[CF_3-(CH_2)_r]_2N-$, $[CF_3-(CH_2)_r]NH-$ or $(CF_3)_2N-(CH_2)_r-$,
B stands for a single bond, O, NH, NR, $CH_2$, C(O)—O, C(O), S, $CH_2$—O, O—C(O), N—C(O), C(O)—N, O—C(O)—N, N—C(O)—N, O—$SO_2$ or $SO_2$—O,
R stands for alkyl having 1 to 4 C atoms,
b stands for 0 or 1,
c stands for 0 or 1,
q stands for 0 or 1, and
r stands for 0, 1, 2, 3, 4 or 5, and
where at least one of b and q stands for 1.

12. A process for preparing a compound according to claim 1, comprising esterifying a fatty acid containing a group Y or a derivative of said fatty acid with a polyol.

13. A composition comprising a compound according to claim 1 and a vehicle which is suitable for a predetermined application.

14. A composition according to claim 13, which is a paint or coating preparation, fire-extinguishing composition, lubricant, washing or cleaning composition, de-icer or hydrophobicising agent for textile finishing or glass treatment.

15. A process for preparing a composition according to claim 13, comprising mixing together the fatty acid ester of a polyol containing at least one group Y with a vehicle which is suitable for a predetermined application.

16. A method of treating a material with a surfactant, comprising treating the material with a compound according to claim 1.

17. A method for subjecting a material, which is a textile, paper, glass, porous building material, or adsorbent, to surface modification, comprising treating the material with a hydrophobicizing agent or oleophobicizing agent, wherein said hydrophobicizing agent or oleophobicizing agent is a compound according to claim 1.

18. A method for subjecting a material, which is selected from the group consisting of textiles, clothing, carpets, carpeting, upholstery in furniture, upholstery in an automobile, non-woven textile materials, leather goods, papers, cardboard articles, wood, wood-based materials, mineral substrates, stone, cement, concrete, plaster, ceramics, glazed tiles, unglazed tiles, earthenware, porcelain, glasses, plastics, and metallic substrates, to an antistatic treatment, comprising treating the material with a compound according to claim 1.

19. A method for modifying a preparation for surface coating, printing inks, paints, coatings lacquers, photographic coatings, special coatings for semiconductor photolithography, photoresists, top antireflective coatings, bottom antireflective coatings, or for modifying an additive preparation for addition to a corresponding preparation, comprising adding a compound according to claim 1 as an additive.

20. A method for achieving a foam stabilizer effect and/or for supporting film formation, optionally in fire-extinguishing foams, comprising applying a compound of claim 1 to a material for which the foam stabilizer effect and/or for supporting film formation is to be achieved.

21. A method for achieving a interface promoter effect or emulsifier effect, optionally for the preparation of fluoropolymers, comprising applying a compound of claim 1 to a material for which the interface promoter effect or emulsifier effect is to be achieved.

22. A compound according to claim 1, wherein
B stands for O, NH, NR, $CH_2$, C(O)—O, C(O), S, $CH_2$—O, O—C(O), N—C(O), C(O)—N, O—C(O)—N, N—C(O)—N, O—$SO_2$ or $SO_2$—O.

* * * * *